(12) United States Patent
Chow

(10) Patent No.: US 9,555,249 B2
(45) Date of Patent: Jan. 31, 2017

(54) ASSESSMENT OF CARDIAC WALL MOTION USING IMPEDANCE MEASUREMENTS

(75) Inventor: Theodore Chow, Saratoga, CA (US)

(73) Assignee: Medtronic, Inc., Minneapolis ( * ) Notice: Subject to any disclaimer, the term of this patent is extended or adjusted under 35 U.S.C. 154(b) by 2212 days.

(21) Appl. No.: 12/551,201

(22) Filed: Aug. 31, 2009

(65) Prior Publication Data

US 2011/0054556 A1 Mar. 3, 2011

(51) Int. Cl.
| | | |
|---|---|---|
| *A61N 1/365* | (2006.01) | |
| *A61N 1/362* | (2006.01) | |
| *A61B 5/053* | (2006.01) | |
| *A61B 5/11* | (2006.01) | |
| *A61B 5/00* | (2006.01) | |
| *A61N 1/372* | (2006.01) | |

(52) U.S. Cl.
CPC ............ *A61N 1/3622* (2013.01); *A61B 5/053* (2013.01); *A61B 5/0538* (2013.01); *A61B 5/1102* (2013.01); *A61B 5/6846* (2013.01); *A61N 1/36521* (2013.01); *A61N 1/37247* (2013.01); *A61B 5/7275* (2013.01); *A61B 2560/0468* (2013.01)

(58) Field of Classification Search
CPC ............ A61B 2560/0468; A61B 5/053; A61B 5/0538; A61B 5/1102; A61B 5/6846; A61B 5/7275; A61N 1/3622; A61N 1/36521; A61N 1/368; A61N 1/37247
USPC ............... 600/508, 509, 547; 607/14, 17, 27
See application file for complete search history.

(56) References Cited

U.S. PATENT DOCUMENTS

| | | | |
|---|---|---|---|
| 6,219,579 B1 | 4/2001 | Bakels et al. | |
| 6,795,732 B2 | 9/2004 | Stadler et al. | |
| 7,203,541 B2 | 4/2007 | Sowelam et al. | |
| 7,346,394 B2 | 3/2008 | Liu et al. | |
| 7,499,749 B2 | 3/2009 | Salo | |
| 2004/0267142 A1* | 12/2004 | Paul | 600/509 |
| 2005/0216067 A1* | 9/2005 | Min et al. | 607/17 |
| 2007/0027489 A1 | 2/2007 | Gill et al. | |
| 2007/0299356 A1 | 12/2007 | Wariar et al. | |
| 2008/0081354 A1 | 4/2008 | Qu et al. | |
| 2008/0097539 A1* | 4/2008 | Belalcazar | 607/17 |
| 2008/0234773 A1* | 9/2008 | Ni et al. | 607/17 |
| 2009/0131996 A1 | 5/2009 | Li | |

FOREIGN PATENT DOCUMENTS

| | | |
|---|---|---|
| WO | WO 2006/042039 A2 | 4/2006 |
| WO | WO 2006/042039 A3 | 4/2006 |

OTHER PUBLICATIONS

International Search Report and Written Opinion from corresponding PCT Application Serial No. PCT/US2010/043539 dated Oct. 15, 2010 (11 pages).

(Continued)

*Primary Examiner* — Edward Moran
*Assistant Examiner* — Pamela M Bays
(74) *Attorney, Agent, or Firm* — Shumaker & Sieffert, P.A.

(57) ABSTRACT

In accordance with the techniques for heart monitoring described in this disclosure, an implantable medical device (IMD) may assess cardiac wall motion using impedance measurements through cardiac leads. As an example, the IMD may calculate an amount or rate of change in impedance due to the motion of a wall of the heart during at least a portion of one cardiac cycle, e.g., systole, in order to assess the strength of systolic contraction.

37 Claims, 16 Drawing Sheets

(56) References Cited

OTHER PUBLICATIONS

International Preliminary Report on Patentability from international application No. PCT/US2010/043539, dated Aug. 25, 2011, 14 pp.
Reply to Written Opinion for international application No. PCT/US2010/043539, filed Jun. 30, 2011, 9 pp.

\* cited by examiner

ASSESSMENT OF CARDIAC WALL MOTION USING IMPEDANCE MEASUREMENTS

TECHNICAL FIELD

This disclosure relates to implantable medical devices, and, more particularly, to devices for monitoring and/or treatment of cardiovascular conditions.

BACKGROUND

A wide variety of implantable medical devices for delivering a therapy or monitoring a physiologic condition have been clinically implanted or proposed for clinical implantation in patients. In some cases, implantable medical devices deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for sensing or delivery of stimulation. For example, electrodes or sensors may be carried at a distal portion of the lead. A proximal portion of the lead that may be coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses or shocks for pacing, cardioversion or defibrillation, via electrodes of one or more implantable leads. In some cases, such an implantable medical device may sense for intrinsic depolarizations of the heart, and control the delivery of such signals to the heart based on the sensing. When an abnormal rhythm is detected, which may be bradycardia, tachycardia or fibrillation, an appropriate electrical signal or signals may be delivered to restore the normal rhythm. For example, in some cases, an implantable medical device may deliver pacing, cardioversion or defibrillation signals to the heart of the patient upon detecting ventricular tachycardia, and deliver defibrillation electrical signals to a patient's heart upon detecting ventricular fibrillation. Pacing signals typically have a lower energy than the cardioversion or defibrillation signals.

Patients with heart failure are, in some cases, treated with cardiac resynchronization therapy (CRT). CRT is a form of cardiac pacing. In some examples, CRT involves delivery of pacing pulses to both ventricles to synchronize their contraction. In other examples, CRT involves delivery of pacing pulses to one ventricle to synchronize its contraction with that of the other ventricular, such as pacing the left ventricle to synchronize its contraction with that of the right ventricle. CRT is one example of a variety of modes cardiac pacing in which stimulation is delivered to one chamber or location at a time that is an interval before or after an event at another chamber or location. The event at the other chamber or location may be the delivery of a pacing pulse to the other chamber or location, or the detection of an intrinsic cardiac depolarization at the other chamber or location.

SUMMARY

In general, this disclosure provides techniques for heart monitoring. In accordance with the techniques described in this disclosure, an implantable medical device (IMD) may assess cardiac wall motion using impedance measurements through cardiac leads. As an example, the IMD may calculate an amount or rate of change in impedance due to the motion of a wall of the heart during at least a portion of one cardiac cycle, e.g., systole, in order to assess the strength of systolic contraction. Monitoring the strength of cardiac contractions in this manner may facilitate an assessment of, as examples, cardiac performance or contractility, the progression of heart failure, the efficacy of a therapy, such as CRT, or the hemodynamic significance of a tachyarrhythmia, such as a ventricular tachyarrhythmia.

In one example, the disclosure provides a method comprising measuring an impedance of an electrical path that includes a portion of a heart wall a plurality of times during at least one portion of a cardiac cycle, the electrical path comprising a first electrode engaged to or within a wall of a chamber of a heart and a second electrode engaged to a housing of an implantable medical device (IMD), and calculating a value indicative of heart wall motion during the portion of the cardiac cycle based on the impedance measurements.

In another example, the disclosure provides a system for assessing cardiac wall motion. The system comprises an impedance measurement module that measures an impedance of an electrical path that includes a portion of a heart wall a plurality of times during at least one portion of a cardiac cycle, the electrical path comprising a first electrode engaged to or within a wall of a chamber of a heart and a second electrode engaged to a housing of an implantable medical device (IMD), and a processor that is configured to calculate a value indicative of heart wall motion during the portion of the cardiac cycle based on the impedance measurements. In another example, the disclosure provides a device for assessing cardiac wall motion. The device comprises an impedance measurement module that measures an impedance of an electrical path that includes a portion of a heart wall a plurality of times during at least one portion of a cardiac cycle, the electrical path comprising a first electrode engaged to or within a wall of a chamber of a heart and a second electrode engaged to a housing of an implantable medical device (IMD), and a processor that is configured to calculate a value indicative of heart wall motion during the portion of the cardiac cycle based on the impedance measurements.

In another example, the disclosure provides a computer-readable medium comprising instructions encoded on the computer-readable medium that, upon execution, cause a processor within an implantable medical device to measure an impedance of an electrical path that includes a portion of a heart wall a plurality of times during at least one portion of a cardiac cycle, the electrical path comprising a first electrode engaged to or within a wall of a chamber of a heart and a second electrode engaged to a housing of an implantable medical device (IMD), and calculate a value indicative of heart wall motion during the portion of the cardiac cycle based on the impedance measurements.

The details of one or more examples are set forth in the accompanying drawings and the description below. Other features, objects, and advantages will be apparent from the description and drawings, and from the claims.

DETAILED DESCRIPTION

Figure 1:
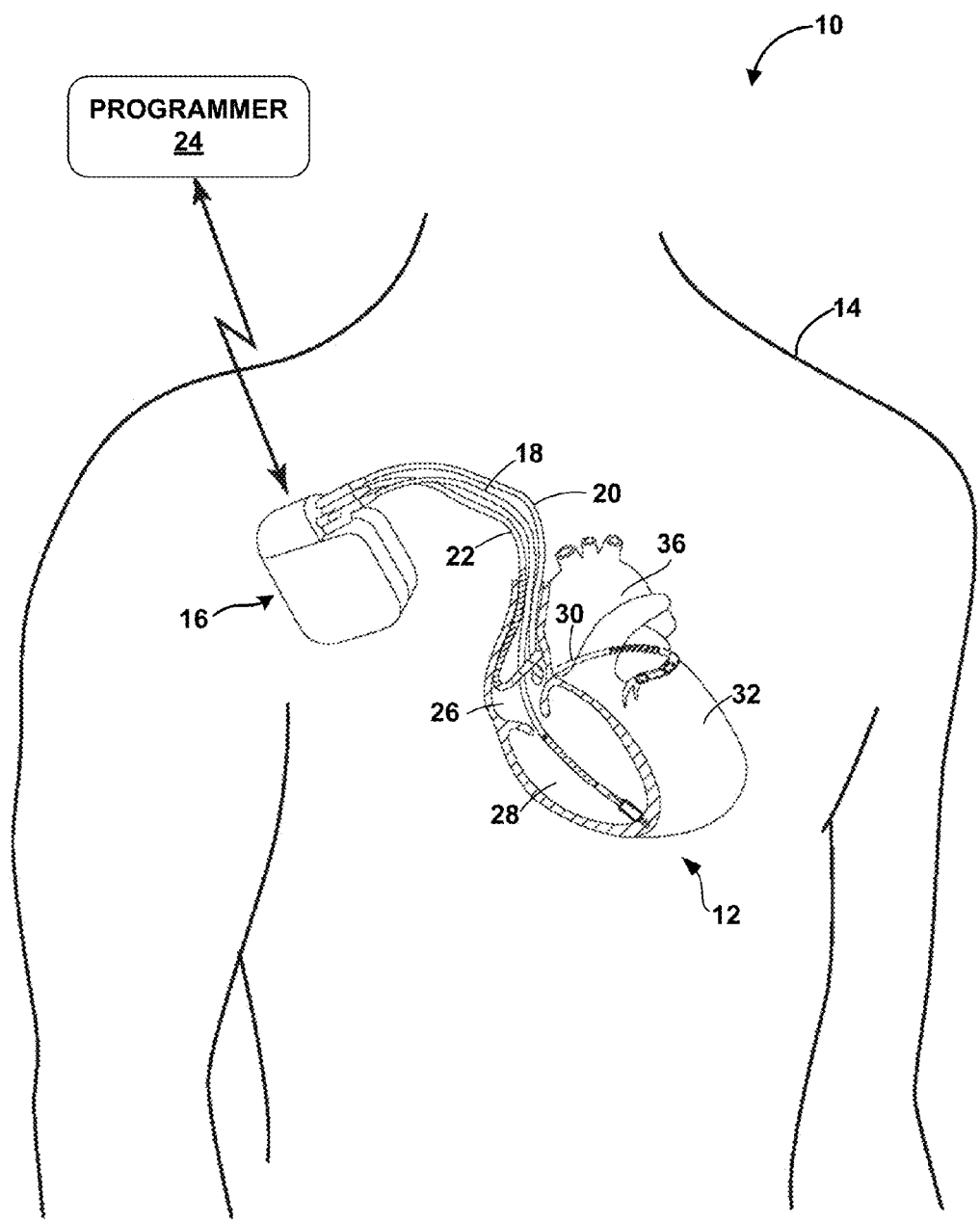
FIG. 1 is a conceptual diagram illustrating an example system that may be used to provide therapy to and/or monitor a heart of a patient.

FIG. 1 is a conceptual diagram illustrating an example system 10 that may be used to monitor and/or provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. In accordance with this disclosure, IMD 16 may measure impedance via one or more of leads 18, 20, and 22 in order to assess cardiac wall motion, as will be described in greater detail below. IMD 16 may provide the measured impedances, data derived therefrom or alerts based thereon to programmer 24 via wireless telemetry.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
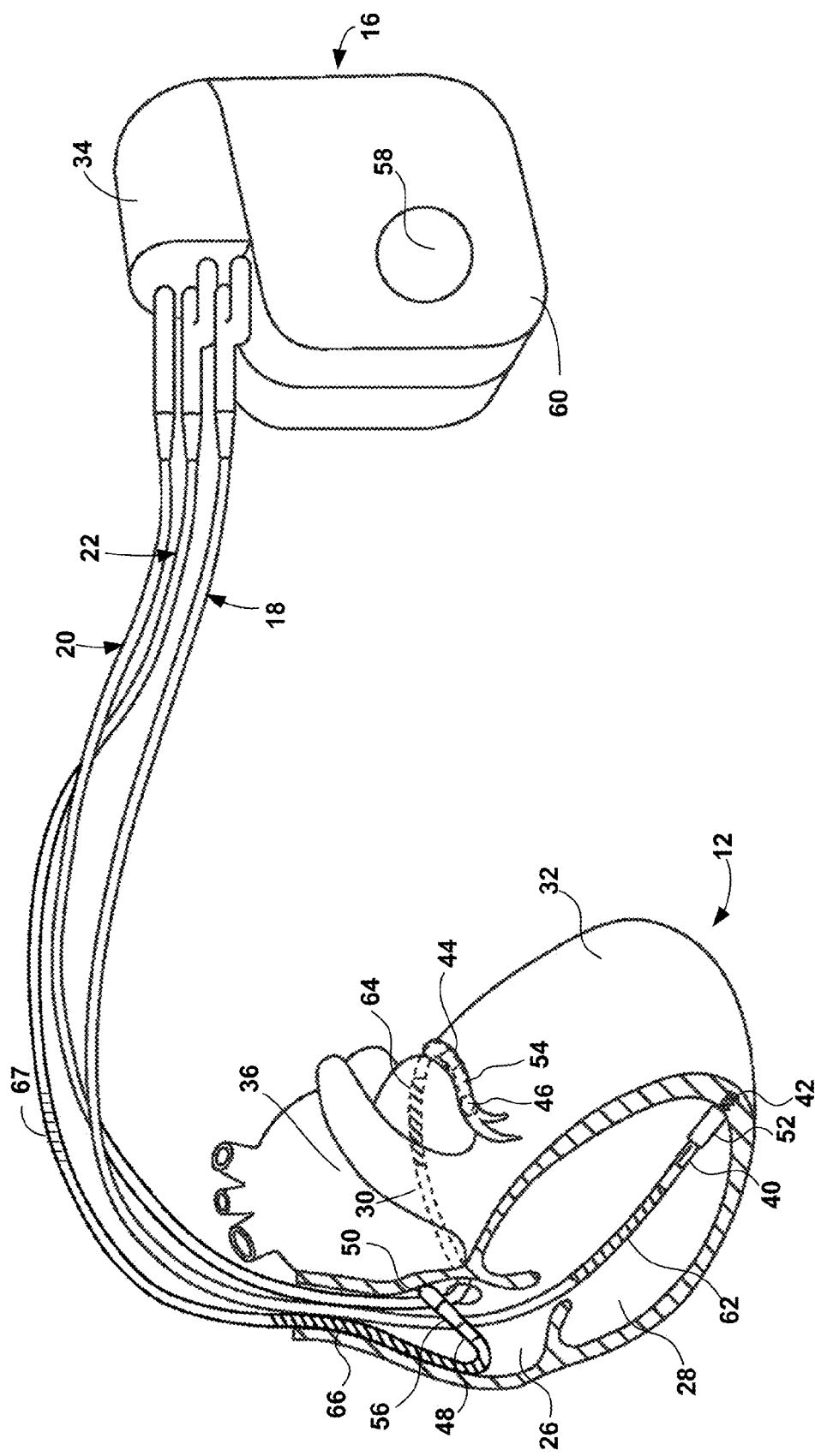
FIG. 2 is a conceptual diagram illustrating the example implantable medical device (IMD) and the leads of the system shown in FIG. 1 in greater detail.

FIG. 2 is a conceptual diagram illustrating IMD 16 and leads 18, 20, and 22 of therapy system 10 in greater detail. Leads 18, 20, 22 may be electrically coupled to a signal generator and a sensing module of IMD 16 via connector block 34.

Each of the leads 18, 20, 22 includes an elongated insulative lead body carrying one or more conductors. Bipolar electrodes 40 and 42 are located adjacent to a distal end of lead 18. In addition, bipolar electrodes 44 and 46 are located adjacent to a distal end of lead 20 and bipolar electrodes 48 and 50 are located adjacent to a distal end of lead 22. Electrodes 40, 44 and 48 may take the form of ring electrodes, and electrodes 42, 46 and 50 may take the form of extendable helix tip electrodes mounted retractably within insulative electrode heads 52, 54 and 56, respectively.

Leads 18, 20, 22 also include elongated intracardiac electrodes 62, 64 and 66 respectively, which may take the form of a coil. In addition, one of leads 18, 20, 22, e.g., lead 22 as seen in FIG. 2, may include a superior vena cava (SVC) coil 67 for delivery of electrical stimulation, e.g., transvenous defibrillation. For example, lead 22 may be inserted through the superior vena cava and SVC coil 67 may be placed, for example, at the right atrial/SVC junction (low SVC) or in the left subclavian vein (high SVC). Each of the electrodes 40, 42, 44, 46, 48, 50, 62, 64, 66 and 67 may be electrically coupled to a respective one of the conductors within the lead body of its associated lead 18, 20, 22, and thereby individually coupled to the signal generator and sensing module of IMD 16.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60.

IMD 16 may sense electrical signals attendant to the depolarization and repolarization of heart 12 via electrodes 40, 42, 44, 46, 48, 50, 58, 62, 64, 66 and 67. The electrical signals are conducted to IMD 16 via the respective leads 18, 20, 22, or in the case of housing electrode 58, a conductor coupled to the housing electrode. IMD 16 may sense such electrical signals via any bipolar combination of electrodes 40, 42, 44, 46, 48, 50, 58, 62, 64, 66 and 67. Furthermore, any of the electrodes 40, 42, 44, 46, 48, 50, 58, 62, 64, 66 and 67 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. For example, electrodes 40, 42, and/or 58 may be used to deliver RV pacing to heart 12. Additionally or alternatively, electrodes 44, 46, and/or 58 may be used to deliver LV pacing to heart 12, and electrodes 48, 50 and/or 58 may be used to deliver RA pacing to heart 12.

Furthermore, IMD 16 may deliver defibrillation pulses to heart 12 via any combination of elongated electrodes 62, 64, 66 and 67, and housing electrode 58. Electrodes 58, 62, 64, 66 may also be used to deliver cardioversion pulses to heart 12. Electrodes 62, 64, 66 and 67 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIGS. 1 and 2. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
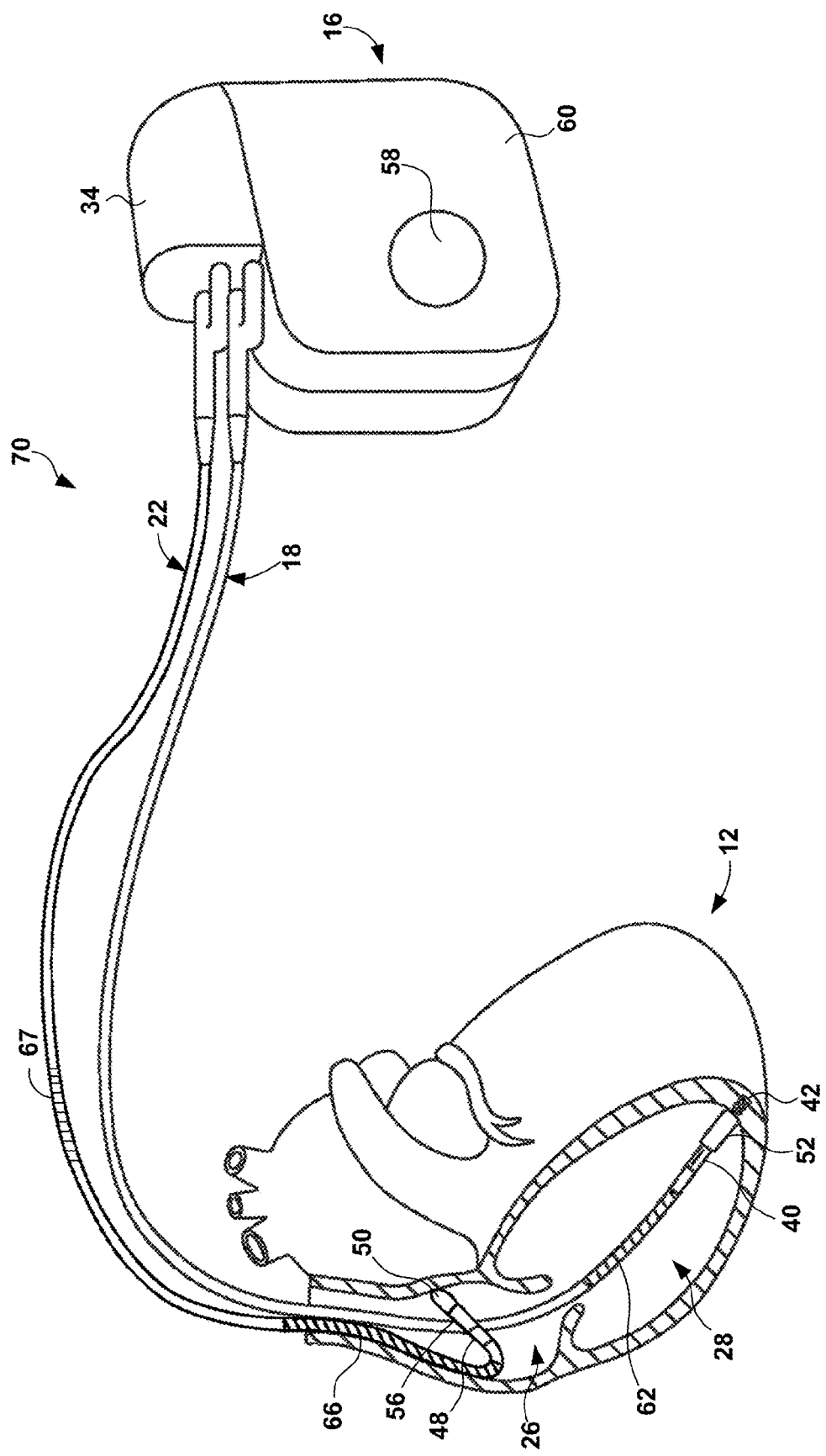
FIG. 3 is a conceptual diagram illustrating another example of a system, which is similar to system shown in FIGS. 1 and 2, but which includes two leads rather than three leads.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. Other examples of therapy systems may include a single lead that extends from IMD 16 into right atrium 26 or right ventricle 28, or two leads that extend into a respective one of the right ventricle 28 and right atrium 26. An example of this type of therapy system is shown in FIG. 3. The example of FIGS. 1 and 2 includes a single electrode per chamber of heart 12 engaged with the wall of heart 12, e.g., free wall, for that chamber. Other examples may include multiple electrodes per chamber, at a variety of different locations on the wall of heart. The multiple electrodes may be carried by one lead or multiple leads per chamber.

In accordance with aspects of this disclosure, a combination of a first electrode within a chamber of the heart or engaged to wall of a chamber of the heart and a second, extra-cardiac electrode may be used to measure the impedance to assess cardiac wall motion, as will be described in detail below. In one example, the second, extra-cardiac electrode may be engaged to the housing of IMD 16, e.g., housing electrode 58. In another example, the second, extra-cardiac electrode may be a coil on a lead that is neither engaged to nor within a chamber of the heart, e.g., SVC coil 67.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12, as well as for measuring impedance to assess cardiac wall motion. In accordance with techniques of this disclosure, at least one of leads 18, 22 may be used in combination with housing electrode 58, an SVC coil (not shown), or another extra-cardiac electrode to measure impedance to assess cardiac wall motion.

Figure 4:
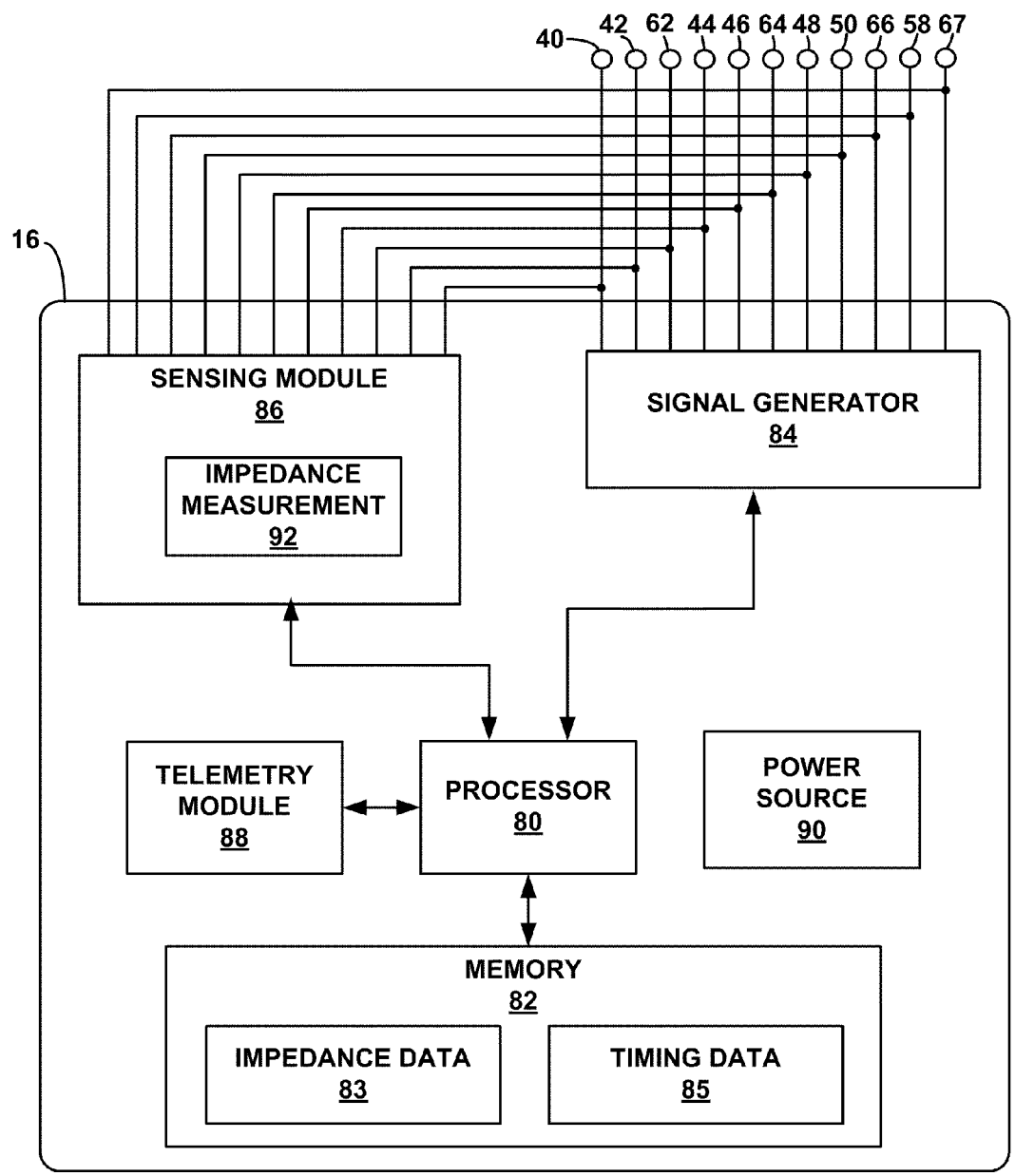
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

In some examples, processor 80 controls signal generator 84 to deliver stimulation therapy to heart 12 according to a selected one or more of therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, 66, and 67 e.g., via conductors of the respective lead 18, 20, 22, or, in the case of housing electrode 58, via an electrical conductor disposed within housing 60 of IMD 16. In some examples, signal generator 84 is configured to generate and deliver electrical stimulation therapy to heart 12. For example, signal generator 84 may deliver defibrillation shocks as therapy to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

Signal generator 84 may include a switch module, and processor 80 may use the switch module to select which of the available electrodes are used to deliver such stimulation. The switch module may include a switch array, switch matrix, multiplexer, or any other type of switching device suitable to selectively couple stimulation energy to selected electrodes.

In some examples, sensing module 86 monitors signals from at least one of electrodes 40, 42, 44, 46, 48, 50, 58, 62, 64, 66 or 67 in order to monitor electrical activity of heart 12. Sensing module 86 may also include a switch module. In some examples, processor 80 may select the electrodes that function as sense electrodes via the switch module within sensing module 86.

Sensing module 86 may include one or more detection channels (not shown), each of which may comprise an amplifier. The detection channels may be used to sense the cardiac signals. Some detection channels may detect cardiac events, such as R- or P-waves, and provide indications of the occurrences of such events to processor 80. One or more other detection channels may provide the signals to an analog-to-digital converter, for processing or analysis by processor 80. In some examples, processor 80 may store the digitized versions of signals from one or more selected detection channels in memory 82 as EGM signals. In response to the signals from processor 80, the switch module within sensing module 86 may couple selected electrodes to selected detection channels, e.g., for detecting events or acquiring an EGM in a particular chamber of heart 12.

During pacing, processor 80 may maintain escape interval counters, such as A-A, V-V, A-V, RV-LV, A-RV, or A-LV interval counters. Processor 80 may reset such counters upon sensing of R-waves and P-waves with detection channels of sensing module 86. Processor 80 may also control signal generator 84 to deliver pacing pulses when the interval counters reach a predetermined value without being reset, and then reset the escape interval counters upon the delivery of the pacing pulses by signal generator 84. In this manner, processor 80 may control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a suspected tachyarrhythmia event, such as ventricular fibrillation or ventricular tachycardia. In some examples, processor 80 may determine that tachyarrhythmia has occurred by identification of shortened R-R (or P-P) interval lengths. An interval length below a threshold may need to be detected for a certain number of consecutive cycles, or for a certain percentage of cycles within a running window, as examples. In some examples, processor 80 may additionally or alternatively employ digital signal analysis techniques to characterize one or more digitized signals from the detection channels of sensing module 86 to detect and classify tachyarrhythmias.

In accordance with this disclosure, IMD 16 and, in particular, impedance measurement module 92 may be configured or controlled to measure the impedance of at least a portion of heart 12 a plurality of times during each of one or more cardiac cycles. Impedance measurement module 92 may measure the impedance of one or more electrical paths that include a portion of the wall of heart 12. Each of the paths may include one or more electrodes carried by a lead, e.g., leads 18, 20, or 22, and an extra-cardiac electrode, e.g., housing electrode 58 or SVC coil 67. The electrodes carried by the leads may be intracardial or epicardial, and may be attached to the heart wall. For each of the paths, the impedance may be measured a plurality of times during at least a portion of the cardiac cycle. In some examples, the impedance for each path is measured a plurality of times during a systolic portion of the cardiac cycle. In some examples, processor 80 may be configured to identify a condition of the heart, e.g., the strength of systolic contraction, the hemodynamic significance of ventricular tachyarrhythmia, or the timing of the movement of the walls of the heart, based on a value indicative of cardiac wall motion derived from the impedance measurements.

In some examples, sensing module 86 and/or processor 80 are capable of measuring impedance for any of a variety of electrical paths that include two or more of electrodes, e.g., at least one of electrodes 40, 42, 44, 46, 48, 50, 58, 62, 64 and 66 in combination with an extra-cardiac electrode. In the illustrated example of FIG. 4, sensing module 86 comprises an impedance measurement module 92, which may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 92, and store measured impedance values in memory 82.

In some examples, processor 80 may perform an impedance measurement by controlling delivery, from signal generator 84, of a voltage pulse between first and second electrodes. Measurement module 92 may measure a resulting current, and processor 80 may calculate an impedance value that includes both a resistive and a reactive component based upon the voltage amplitude of the pulse and the measured amplitude of the resulting current. In other examples, processor 80 may perform an impedance measurement by controlling delivery, from signal generator 84, of a current pulse between first and second electrodes.

Measurement module 92 may measure a resulting voltage, and processor 80 may calculate an impedance value based upon the current amplitude of the pulse and the measured amplitude of the resulting voltage. Measurement module 92 may include circuitry for measuring amplitudes of resulting currents or voltages, such as sample and hold circuitry.

In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue of heart 16.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

During a cardiac cycle, the shape and position of the wall of the heart may change. As the shape and position of the wall of the heart changes, and as the wall of the heart to which one or more leads are affixed moves, the impedance measured from an electrode placed at the distal end of the lead(s) (e.g., the distal tip of a lead) to a reference point (e.g., IMD 16 or another extra-cardiac electrode) may change. Thus, cardiac wall motion data may be derived from a difference between a first impedance measurement and a second impedance measurement for an electrical path comprising a wall of the heart during at least one portion of a cardiac cycle, e.g., a systolic period of the cardiac cycle.

In some examples, the change in impedance may be used as a marker for the strength of systolic contraction. That is, as the impedance measurement changes, the change may be indicative of a weakening of systolic contraction of heart 12. Such a weakening may be a precursor to or indicative of a severe heart condition.

As illustrated in FIG. 4, in addition to program instructions, memory 82 may store impedance data 83 and timing data 85. Processor 80 may store measured impedances for each of a plurality of paths, and values indicative of heart wall motion derived therefrom, within memory 82 as impedance data 83. Processor 80 may control impedance measurement module 92 to measure the impedances during a portion of the cardiac cycle based on timing data 85. Timing data 85 may specify an interval relative to an intrinsic (sensed) or paced depolarization for the measurement of a plurality of impedances. For example, timing data 85 may specify two or more impedance measurements beginning 20 milliseconds after the depolarization. Providing such a delay may help remove any artifacts caused by the depolarization. In some examples, a timing window for the impedance measurements may extend for a fraction of the ventricular cycle length, e.g., 60%, or the time corresponding to systole.

Figure 5:
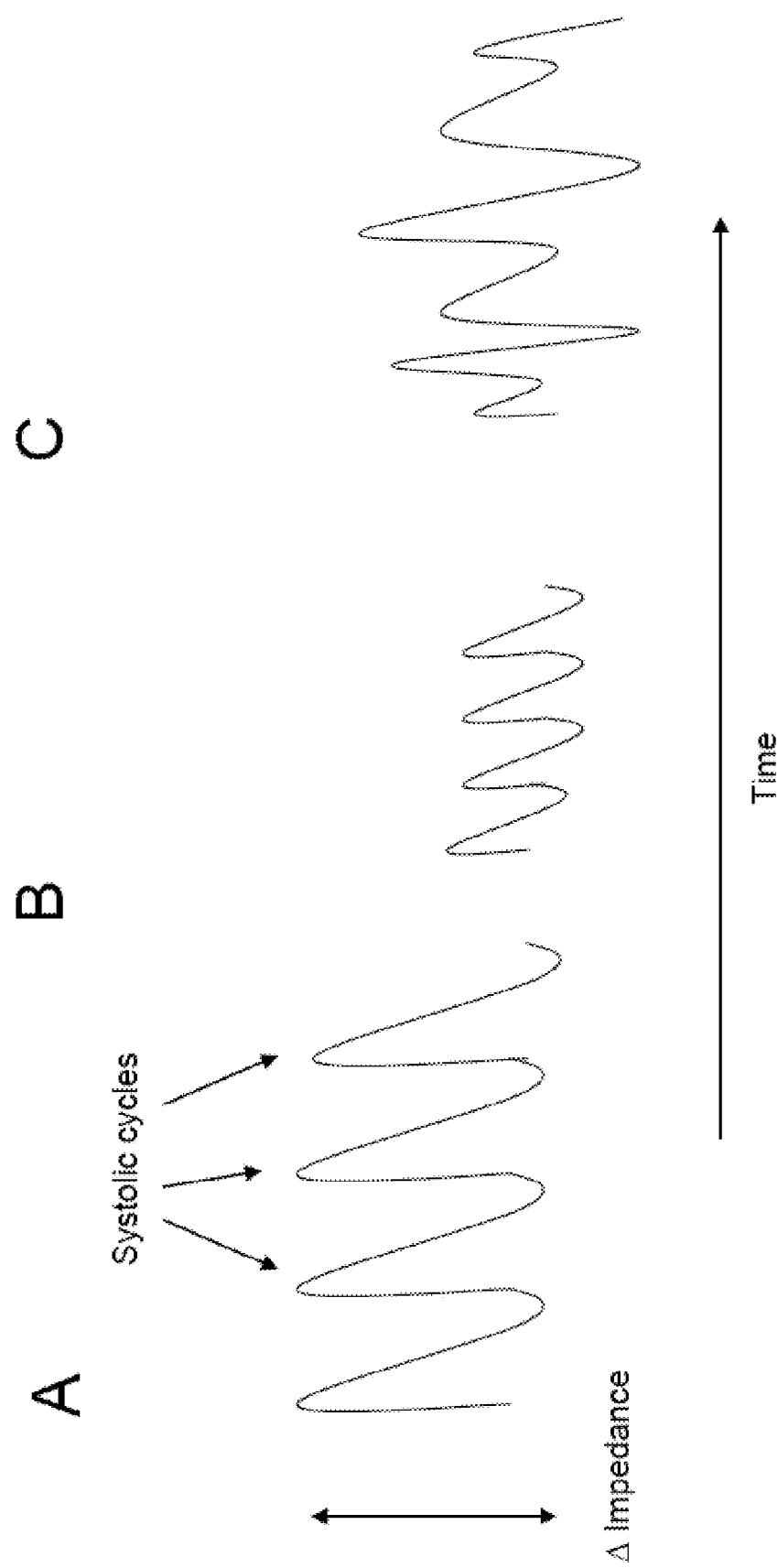
FIG. 5 is a conceptual illustration of variation of impedance as a function of cardiac wall motion and during different cardiac conditions.

FIG. 5 is a conceptual illustration of variation of impedance as a function of cardiac wall motion and during different cardiac conditions. In FIG. 5, the x-axis represents time that includes multiple systolic periods, and the y-axis represents impedance of an example path that includes a wall of a heart. FIG. 5 depicts three examples of impedance measurements, labeled "A," "B," and "C." As the shape and position of the wall of the heart changes, and as the wall of the heart to which one or more leads are affixed moves, the impedance measured from an electrode placed at the distal end of the lead(s) (e.g., the distal tip of a lead) to a reference point (e.g., IMD 16 or another electrode) may change. In example "A," the heart wall motion, as derived from the size of the impedance change during each systole, suggests good contractile force (i.e., cardiac output.) In addition, the uniformity of the impedance plots in example "A" suggests that each systole is substantially homogeneous. In example "B," the size of the wall muscle excursion as derived from the size of the impedance change during each systole is significantly less than as shown in example "A," despite an overall heart rate that is similar to the heart rate in example "A." As seen in example "C," the systolic changes in impedance lack uniformity. The lack of uniformity to the impedance changes suggests ventricular fibrillation or polymorphic ventricular tachycardia (VT), rather than monomorphic VT.

Assuming that each of examples A, B and C was measured during a detected tachyarrhythmia, with respect to example "A," it may be desirable to first treat the patient with several rounds of anti-tachycardia pacing therapy prior to delivering shock therapy. With respect to example "B," the patient may expected to have impending hemodynamic collapse, thus shock therapy may be delivered immediately. With respect to example "C," the patient is likely to have ventricular fibrillation or polymorphic ventricular tachycardia and should also be provided shock therapy immediately. In this manner, impedance measurements of a wall of a heart may be used to assess cardiac wall motion in order to guide therapy.

As can be seen, the impedance of a path that includes a portion of the heart wall may as a function of the movement of the heart wall. IMD 16 measures the impedance of the path a plurality of times during at least a portion of a cardiac cycle. IMD 16 determines a value indicative of wall motion for the path and the cycle based on the plurality of impedance measurements for the path during the cycle. IMD 16 may determine the value based on the difference, average, or variability of the values, as examples. The value may be a slope of the measured impedances, as another example.

A change in the values indicative of heart wall motion or the variability of the values may provide an indication of worsening of clinical condition, e.g., worsening heart failure. In another example, a change in the values indicative of heart wall motion or the variability of the values may be used to assess the hemodynamic significance of ventricular tachyarrhythmias for the purpose of guiding device therapy, e.g., withholding therapy, employing anti-tachycardia pacing algorithms prior to shock, or shocking directly. In another example, the values indicative of heart wall motion may be used for cardiac resynchronization, as will be described in more detail below.

Electrodes may be attached, affixed, implanted, or otherwise engaged to the wall of the heart at various locations. Referring to FIG. 1, in some examples, electrodes may be attached to a region adjacent to the free wall of left ventricle 32 of heart 12 and/or right ventricle 28, with housing electrode 58 on IMD 16, SVC coil 67, or another extra-cardiac electrode used as the reference point for impedance measurements.

In a further example, electrodes may be attached to left atrium 36 and/or right atrium 26 with housing electrode 58 on IMD 16, SVC coil 67, or another extra-cardiac electrode used as the reference point for impedance measurements.

It should be noted that only a few of the many possible locations for electrode placement have been described above. There are numerous locations of heart 12 that may be suitable for electrode placement in order to measure impedance for assessment of cardiac wall motion.

Figure 6:
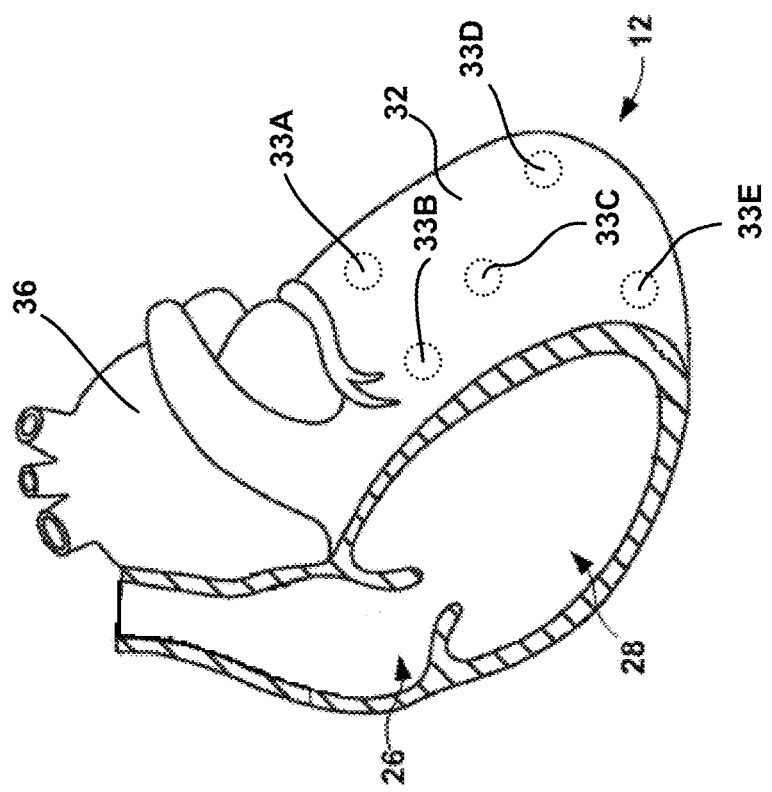
FIG. 6 is a schematic diagram illustrating example electrode placements on or within a left ventricle of a heart.

FIG. 6 is a schematic diagram illustrating example electrode placements on left ventricle 32 of heart 12. In the example of FIG. 6, multiple electrodes may be attached to a number of regions 33A-33E ("regions 33") adjacent to the free wall of left ventricle 32 of heart 12. For simplicity, no leads are depicted in FIG. 6, and only some of regions 33 suitable for electrode attachment are shown. Those skilled in the art will recognize that other regions 33 not shown may also be suitable for electrode attachment. It should be noted that it may be desirable to attach multiple electrodes within right atrium 26, left atrium 36, and right ventricle 28 of heart 12. However, for simplicity, only regions 33 have been shown with respect to left ventricle 32 of heart 12 in FIG. 6. By attaching a number of electrodes at regions 33, for example, multiple impedance measurements may be taken between those electrodes and an extra-cardiac electrode, e.g., housing electrode 58 or SVC coil 67, for one or more walls of the heart, e.g., the wall of left ventricle 32. Multiple impedance measurements taken for one or more walls of the heart may provide a more accurate assessment of the condition of the heart, e.g., systolic contraction, than that of a single impedance measurement.

One example may use a 4-wire, or Kelvin, sensing arrangement. In an example 4-wire arrangement, IMD 16 sources an electrical signal, such as a current, to a first electrode via a first lead, while a second electrode via a second lead sinks the electrical signal. IMD 16 then measures the voltage between a third electrode and a fourth electrode via their respective leads. IMD 16 may measure the impedance of a path including a portion of the heart wall by using a known value of the electrical signal sourced and the measured voltage.

In some examples, the leads carrying electrodes that are attached at regions 33 may be leads such as leads 18, 20, 22 that are designed to provide electrical stimulation therapy to heart 12. In other examples, the leads carrying electrodes that are attached at regions 33 may be leads that provide no electrical stimulation therapy to heart 12. That is, the leads may be designed and implanted specifically for determining the motion of the wall of the heart. Because the leads do not provide electrical stimulation therapy to the heart, and thus carry less current, the leads may be designed to have a smaller cross-sectional area than leads that do provide electrical stimulation therapy. The smaller cross-sectional area may allow the leads to be placed in a number of cardiac veins that leads designed to provide electrical stimulation therapy would be unable to fit through, thereby allowing additional impedance measurements to be taken.

Figure 7:
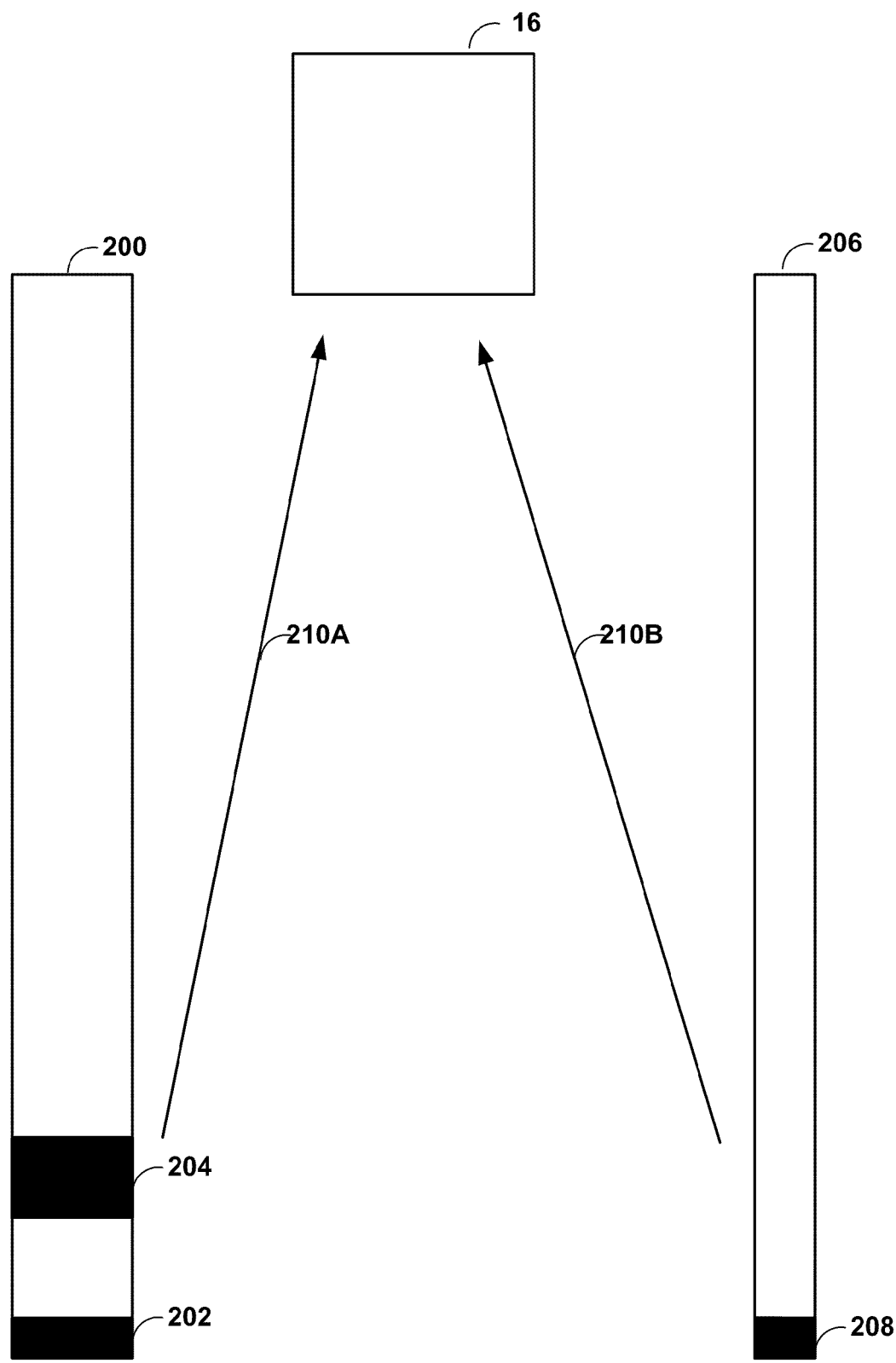
FIG. 7 is conceptual diagram illustrating leads configured for detecting impedance in conjunction with an IMD.

FIG. 7 is a conceptual diagram illustrating a standard IMD lead and a lead specifically designed for impedance measurements to assess heart wall motion. In FIG. 7, standard IMD or pacemaker lead 200 is depicted with tip electrode 202 and ring electrode 204. Tip electrode 202 may act as a signal source for an impedance measurement. In other examples, as illustrated in FIG. 7, ring electrode 204 may act as a signal source for an impedance measurement. In the illustrated example, an electrode on IMD 16 acts as the signal return for impedance measurements.

Lead 206 is a lead specifically designed for determination of impedance as a primary function. Lead 206 includes a single electrode, tip electrode 208, at the distal end of lead 206 that sources a signal for the measurement of impedance. As seen graphically in FIG. 7, lead 206 is thinner than lead 200, thereby allowing access to smaller cardiac veins.

In FIG. 7, arrows 210A and 210B are used to indicate that IMD 16 may be the return, reference or ground for the impedance measurement. In other examples, IMD 16 or another extracardiac electrode may be the source, with one or more cardiac electrodes being the return, reference or ground. In one example, several of these leads 206 may be placed in various cardiac veins traversing the global anatomy of the left ventricle, for example. By using multiple leads 206 specifically designed for determination of pacing impedance, assessment of interventricular (dys)synchrony may be more precise then if standard IMD leads 200 were used. It should be noted that because low pacing amplitudes are used for impedance measurements, phrenic nerve stimulation, which ordinarily limits placement of pacing leads, is unlikely to be an issue.

Referring again to FIG. 4, processor 80 may execute instructions that compare a value indicative of heart wall motion, e.g., the overall change in value of the impedance measured and/or the rate of change in the impedance measured during at least a portion of a cardiac cycle, to baseline or threshold values stored as impedance data 83 in memory 82. In some examples, a baseline value may be patient-specific. For example, during an initial clinician visit, a patient may have undergone an evaluation in order to determine baseline impedance values that may be stored as impedance data 83. In other examples, a baseline value may be determined based on an average of a number of previous values. In other examples, the baseline value may be based on a model given certain characteristics of a patient, e.g., sex, age, height, and weight.

In such a manner, aspects of this disclosure may provide patient monitoring. In some examples, if the value indicative of heart wall motion during a cardiac cycle, e.g., the overall change in the value of impedance and/or the rate of change in the impedance during the systolic portion of the cardiac cycle, deviates beyond the baseline value, the patient and/or clinician may be alerted.

For example, over a systolic period, signal generator 84 may generate a plurality of electrical signals, e.g., a current pulse, between first and second electrodes. Measurement module 92 may measure over the systolic period, e.g., around the time of a sensed or paced depolarization, the resulting voltage, and processor 80 may calculate impedance values based upon the current amplitude of the pulses and the measured amplitudes of the resulting voltage. Based on the plurality of measured impedance values during the systolic period, processor 80 may determine a value indicative of heart wall motion, such as the difference between, change in, or slope of the impedance values. The value indicative of heart wall motion may then be stored in memory 82. In contrast to many implantable medical devices in which measurements are taken only a few times per day or a few times per hour, examples of the present invention measure impedance a plurality of times during a cardiac cycle and, in some examples, a plurality of times during a portion of the cardiac cycle, e.g., the systolic portion.

In some examples, processor 80 may then execute instructions, e.g., instructions stored in memory 82, that retrieve a baseline value stored as impedance data 83 in memory 82 and compare value indicative of heart wall motion to the baseline value. The value indicative of heart wall motion derived from the plurality of measured impedances during at least a portion of the cardiac cycle may be used in a patient monitoring role. The patient monitoring role may, in one example, include a patient and/or physician alert system. By way of example, based on the comparison, processor 80 may execute instructions that generate an alarm. IMD 16 may communicate with an external device, e.g., programmer 24 or a networked computing device, via wireless communication to alert the patient and/or clinician that the condition of the patient's heart has changed and that the patient may require medical attention. IMD 16 may communicate to programmer 24 via telemetry module 88. The alarm may be transmitted to programmer 24 via telemetry module 88. In some examples, the alarm may be an audible alarm, while in other examples the alarm may be a visual alarm, such as a text message or color-coded alarm displayed on programmer 24. In other examples, the alarms may be combined, e.g., an audible alarm combined with a text-based alarm message indicating the impedance measurements. In response to the alarm, the patient or a clinician may respond appropriately based on the information conveyed via programmer 24.

Telemetry module 88 includes any suitable hardware, firmware, software, or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

As mentioned above, the impedance-based value indicative of heart wall motion may additionally or alternatively be used to optimize or otherwise adjust cardiac resynchronization therapy (CRT). For example, processor 80 may adjust the timing between depolarizations of the ventricles, e.g., by adjusting one or more A-V or V-V intervals, and controlling delivery of pacing pulses by signal generator 84 based on the adjusted intervals, in order to improve, optimize, or achieve a desired target for the value indicative of heart wall motion. In some cases, the heart movement may not be at the same time as when the heart becomes electrically stimulated. In some examples, processor may identify a fiducial point in the cardiac mechanical cycle for each of a plurality of locations based on a plurality of impedance measurements for each of a plurality of paths. An example fiducial point is onset of mechanical contraction. Based on the relative timing of the fiducial points, processor 80 may adjust the timing between depolarizations of the ventricles, e.g., by adjusting one or more A-V or V-V intervals.

Figure 8:
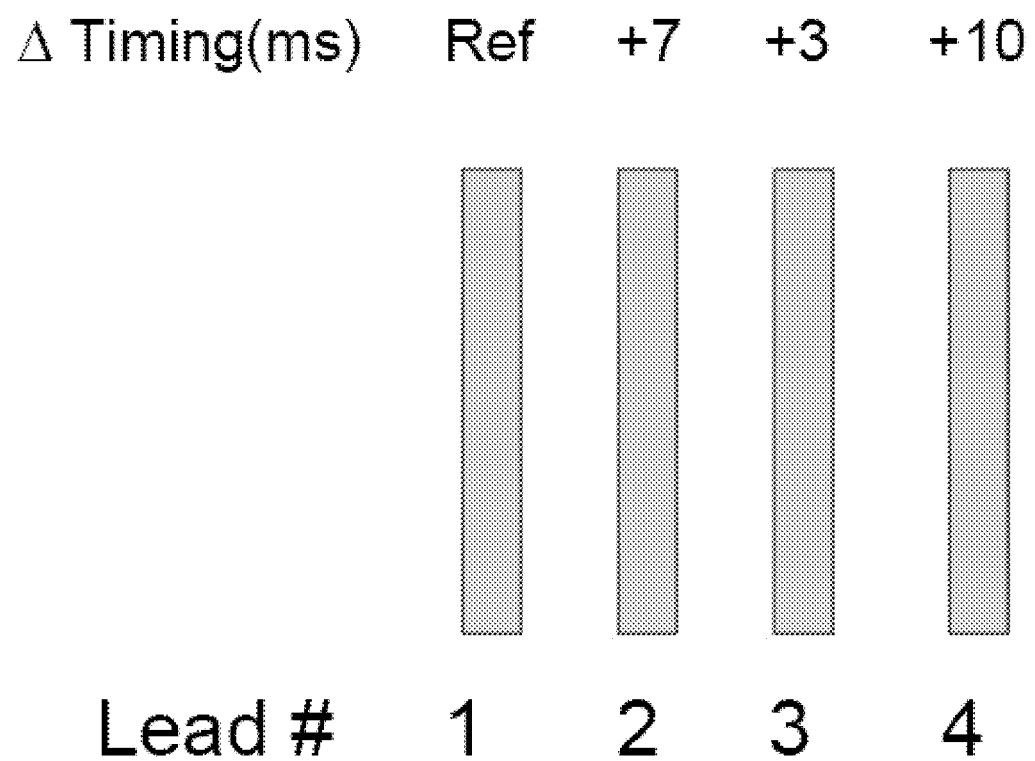
FIG. 8 is a conceptual diagram illustrating the relative timing of cardiac wall motion at a plurality of locations as detected by leads respectively positioned at the locations.

FIG. 8 is a conceptual diagram illustrating the relative timing of cardiac wall motion at a plurality of locations as detected by leads respectively positioned at the locations. Lead numbers 1-4 include respective electrodes at different cardiac locations for measuring impedance of four paths that include the respective electrodes and an extracardiac electrode. The different locations may be cardiac wall locations in the same chamber or different chambers of heart. Fiducial points in the mechanical cardiac cycle for each location may be identified as described above. FIG. 8 illustrates the timing difference between the fiducial points. Lead number 1 is the reference lead. Lead number 2 has a difference in timing of 7 ms relative to lead number 1, e.g., the fiducial point, such as onset of contraction occurred 7 ms later at the heart wall location associated with lead 2 than the heart wall location associated with lead 1. Lead number 3 has a difference in timing of 3 ms. Lead number 4 has a difference in timing of 10 ms.

By measuring the timing at the various leads, techniques of this disclosure allow for assessment of global dys-synchrony (measured in ms) as compared to the reference lead, i.e., lead number 1. Summing the dys-synchrony across all leads may yield a global dys-synchrony that may be used as an index of intra-ventricular cardiac dys-synchrony. Programming changes may then be made for CRT, e.g., changing one or more V-V or A-V intervals, in order to minimize the global (i.e., summed) dys-synchrony across all leads.

For example, a threshold value of global dys-synchrony may be stored as timing data 85 in memory 82. Using the techniques of this disclosure, impedance measurements taken by two or more leads may be used to derive the timing of the onset of cardiac motion at two or more locations. Processor 80 may then execute instructions that sum the changes in timing measured by two or more leads in order to determine a global dys-synchrony. Processor 80 may then execute instructions that compare the summed global dys-synchrony with the threshold value or optimal timing stored in memory 82. Based on the comparison, CRT programming changes in the timing cycles may then be made in order to minimize the global dys-synchrony across all leads.

In one example, the optimal timing may be based on patient-specific measurements. Regardless, deviations between the timings at a plurality of heart wall locations may suggest a need to re-optimize the programming of IMD 16.

In other examples, as described above, based on the impedance-based value indicative of heart wall motion (e.g., overall change in value or rate of change in impedance during the systolic phase of a cardiac cycle), a determination may be made regarding global systolic resynchronization. If processor 80 determines that global systolic resynchronization has not been achieved, e.g., due to a decrease in the value indicative of heart wall motion, adjustment of the programming of CRT to achieve global systolic resynchronization may be undertaken. The adjustment may include adjustement of A-V or V-V intervals in order to improve or optimize global synchrony as assessed through the impedance sensing leads. In such a manner, IMD 16 may automatically adjust the timing cycles and/or other programming features, e.g., amplitudes, pulse widths, frequency, or electrode polarities, to re-optimize global cardiac resynchronization based upon impedance measurement derived assessment of wall motion data.

In some examples, IMD 16 may communicate with an external device, e.g., programmer 24, via wireless communication to alert the patient and/or clinician of changes in cardiac resynchronization and/or of the need to re-optimize the programming of IMD 16, as assessed through impedance measurement derived wall motion data. Telemetry module 88 may transmit the alert to programmer 24, and programmer 24 may then alert the patient or physician via an audible or visual alert.

In another example, the value indicative of heart wall motion (e.g., the overall change in impedance or the rate of change in impedance during the systolic portion or phase of the cardiac cycle) may be used to determine whether cardiac systolic deterioration is progressing. As mentioned above, values indicative of heart wall motion may be stored as impedance data 83 in memory 82. Over time, these values may show a trend indicating that cardiac systolic deterioration is progressing. Processor 80 may execute instructions periodically and/or based on a command issued via programmer 24 by a user to compare a value indicative of heart wall motion to the previously stored data representative of a trend of such values over time, e.g., an average of previous values. A user, e.g., a clinician, may retrieve the impedance data 83 from IMD 16 via programmer 24 by way of their respective telemetry modules. The impedance data, e.g., the values indicative of heart wall motion, may then be graphed, plotted, displayed, or otherwise reported thereby providing clinically actionable diagnostic information to a clinician.

As mentioned above, one or more leads may be used to measure the impedance of a path including a portion of the heart wall for one or more chamber of heart 12. In some examples, paced depolarizations, or depolarizations sensed through one or more leads, may be used for timing purposes to establish a window in which to measure impedance and detect movement in the cardiac wall, e.g., during the systolic phase. In some examples, data defining this window relative to a depolarization is stored as timing data 85 in memory 82. In some examples, the rate of sensed depolarizations, or heart rate, may be used in order to discriminate impedance changes that are due to cardiac motion, i.e., changes that occur with a periodicity similar to the heart rate, from changes in impedance due to other artifacts, e.g., artifacts resulting from respiration or body motion.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 9:
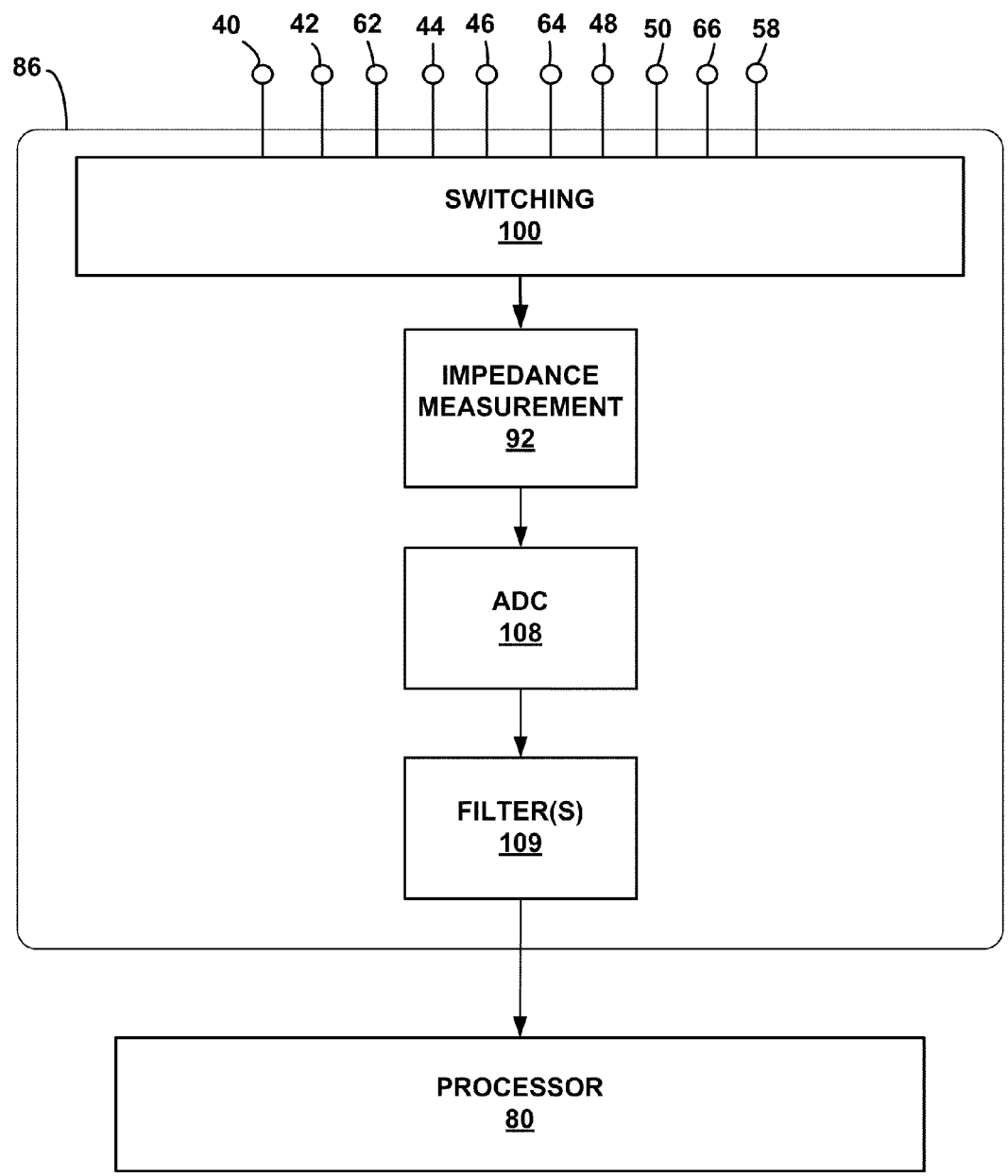
FIG. 9 is a block diagram of an example configuration of an electrical sensing module.

FIG. 9 is a block diagram of an example configuration of electrical sensing module 86. As shown in FIG. 9, electrical sensing module 86 includes multiple components including switching module 100, analog to digital converter (ADC) 108, and, optionally, one or more filters 109. Filters 109 may be used to reduce or eliminate noise, e.g., noise produced by patient respiration or body motion. Switching module 100 may, based on control signals from processor 80, control which of electrodes 40, 42, 44, 46, 48, 50, 58, 62, 64 and 66 is coupled to impedance measurement module 92 at any given time. Switching module 100 may comprise a multiplexer, and in some examples may comprise a transistor array, an array of microelectromechanical switches, or the like.

As illustrated in FIG. 9, impedance measurements collected, calculated, and/or measured by impedance measurement module 92 may be digitized by ADC 108. In some examples, digitized versions of voltage or current values measured by impedance measurement module 92 from ADC 108 may be filtered by one or more optional filters 109. Filter(s) 109 may remove changes in impedance that may be the result of noise and/or other artifacts, e.g., patient respiration, patient movement, or the like. In such a manner, the filtered signal may accurately reflect the change in impedance that is the result of cardiac wall motion. Processor 80 may then receive filtered, digitized versions of voltage or current values measured by impedance measurement module 92 from filter(s) 109, and determine impedances for the electrode combinations based on the digitized values.

Figure 10:
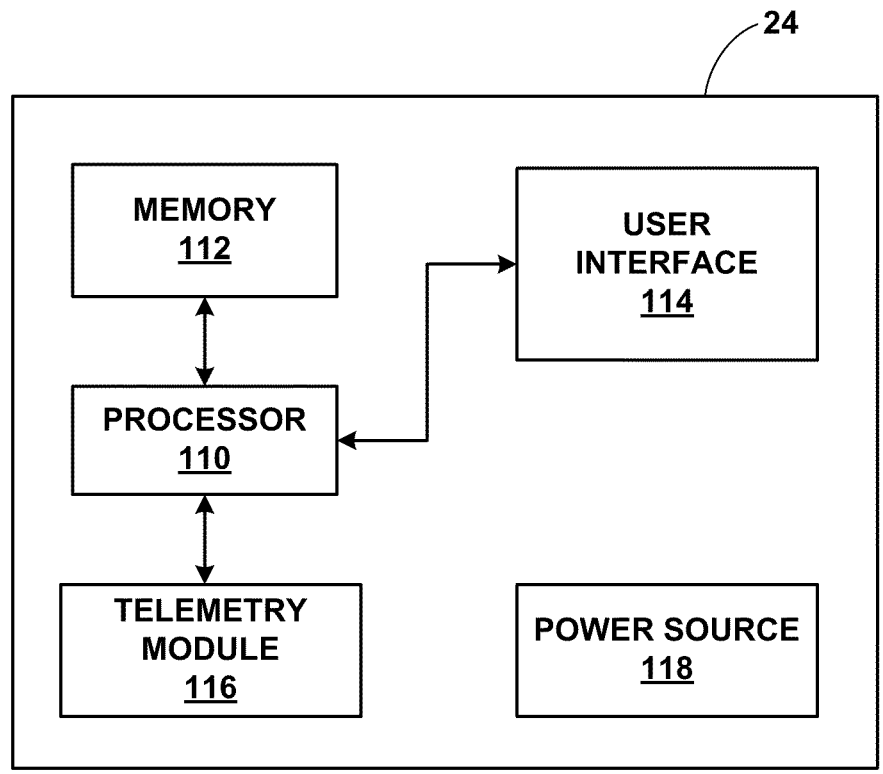
FIG. 10 is functional block diagram illustrating an example configuration of the programmer of FIG. 1.

FIG. 10 is functional block diagram illustrating an example configuration of programmer 24. As shown in FIG. 10, programmer 24 may include a processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present graphical user interface to a user, and a keypad or another mechanism for receiving input from a user.

The user, e.g., a clinician, may define threshold or baseline values that may be stored as impedance data 83 in memory 82 within IMD 16. The user may also program the window for measuring impedance subsequent to a depolarization, data controlling which may be stored as timing data 85 in memory 82. The user may also use programmer 24 to adjust or control other aspects of the impedance measurements performed by IMD 16. For example, the user may use programmer 24 to program the number of test pulses, the timing of test pulses, the parameters of each test pulse, the electrodes to use for measuring, or any other aspects of the impedance measurements. In this manner, the user may be able to finely tune the impedance measurements to test the specific condition of heart 12. In addition, the user may receive an alert from IMD 16 indicating a potential issue with the patient's heart via programmer 24.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 4).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 110 of programmer 24 and/or one or more processors of one or more networked computers may perform all or a portion of the techniques described herein with respect to processor 80 and IMD 16. For example, processor 110 or another processor may receive voltages or currents measured by IMD 16 to calculate impedance measurements, or may receive impedance measurements from IMD 16. Processor 110 or another processor may determine values indicative of cardiac wall motion based on the impedance measurements and assess the condition of a patient using any of the techniques described in this disclosure. Power source 118 delivers operating power to the components of programmer 24.

Figure 11:
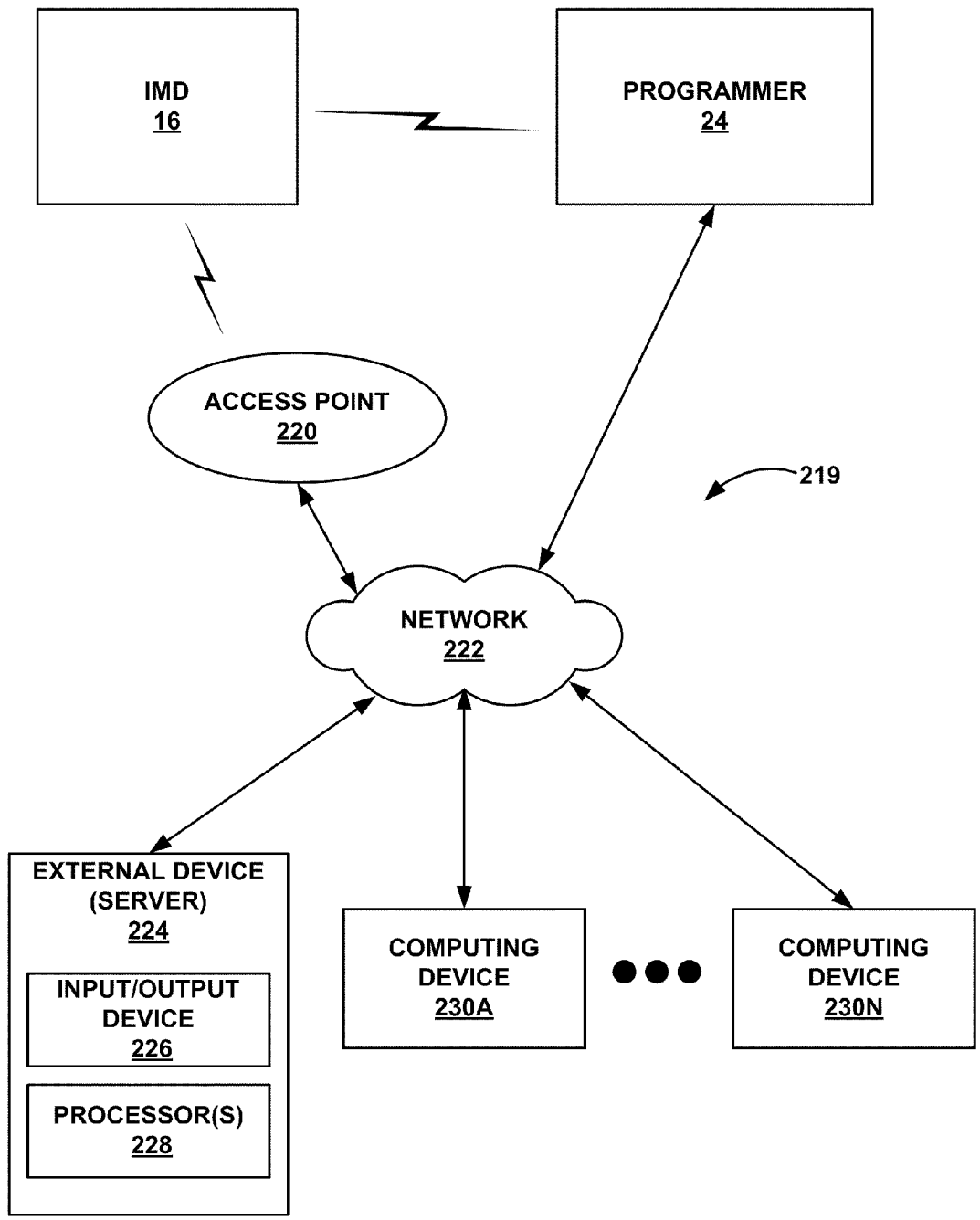
FIG. 11 is a block diagram illustrating an example system that includes a server and one or more computing devices that are coupled to the IMD and the programmer shown in FIG. 1 via a network.

FIG. 11 is a block diagram illustrating an example system 219 that includes an external device, such as a server 224, and one or more computing devices 230A-230N, that are coupled to the IMD 16 and programmer 24 shown in FIG. 1 via a network 222. In this example, IMD 16 may use its telemetry module 88 to communicate with programmer 24 via a first wireless connection, and to communication with an access point 220 via a second wireless connection. In the example of FIG. 11, access point 220, programmer 24, server 224, and computing devices 230A-230N are interconnected, and able to communicate with each other, through network 222. In some cases, one or more of access point 220, programmer 24, server 224, and computing devices 230A-230N may be coupled to network 222 through one or more wireless connections. IMD 16, programmer 24, server 224, and computing devices 230A-230N may each comprise one or more processors, such as one or more microprocessors, DSPs, ASICs, FPGAs, programmable logic circuitry, or the like, that may perform various functions and operations, such as those described herein.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14 and may comprise one or more programming units and/or computing devices (e.g., one or more monitoring units) that may perform various functions and operations described herein. For example, access point 220 may include a home-monitoring unit that is co-located with patient 14 and that may monitor the activity of IMD 16.

In some cases, server 224 may be configured to provide a secure storage site for data that has been collected from IMD 16 and/or programmer 24. Network 222 may comprise a local area network, wide area network, or global network, such as the Internet. In some cases, programmer 24 or server 224 may assemble data in web pages or other documents for viewing by trained professionals, such as clinicians, via viewing terminals associated with computing devices 230A-230N. The illustrated system of FIG. 11 may be implemented, in some aspects, with general network technology and functionality similar to that provided by the Medtronic CareLink® Network developed by Medtronic, Inc., of Minneapolis, Minn.

In some examples, processor 228 of server 224 may be configured to receive voltages or currents measured by IMD 16 to calculate impedance measurements, or may receive impedance measurements from IMD 16. Processor 228 or may determine values indicative of cardiac wall motion based on the impedance measurements and assess the condition of a patient using any of the techniques described in this disclosure. Processor 228 may provide alerts to users, e.g., to the patient via access point 220 or to a clinician via one of computing devices 230, based on identifying change, e.g., worsening) in patient condition using impedance-based values indicative of heart wall motion. Processor 228 may suggest to a clinician, e.g., via programmer 24 or a computing device 230, a change in a therapy, such as CRT, based on impedance-based values indicative of heart wall motion. Processor 228 may also adjust or control the delivery of therapy by IMD 16, e.g., CRT or anti-tachyarrhythmia therapy, via network 222.

Figure 12:
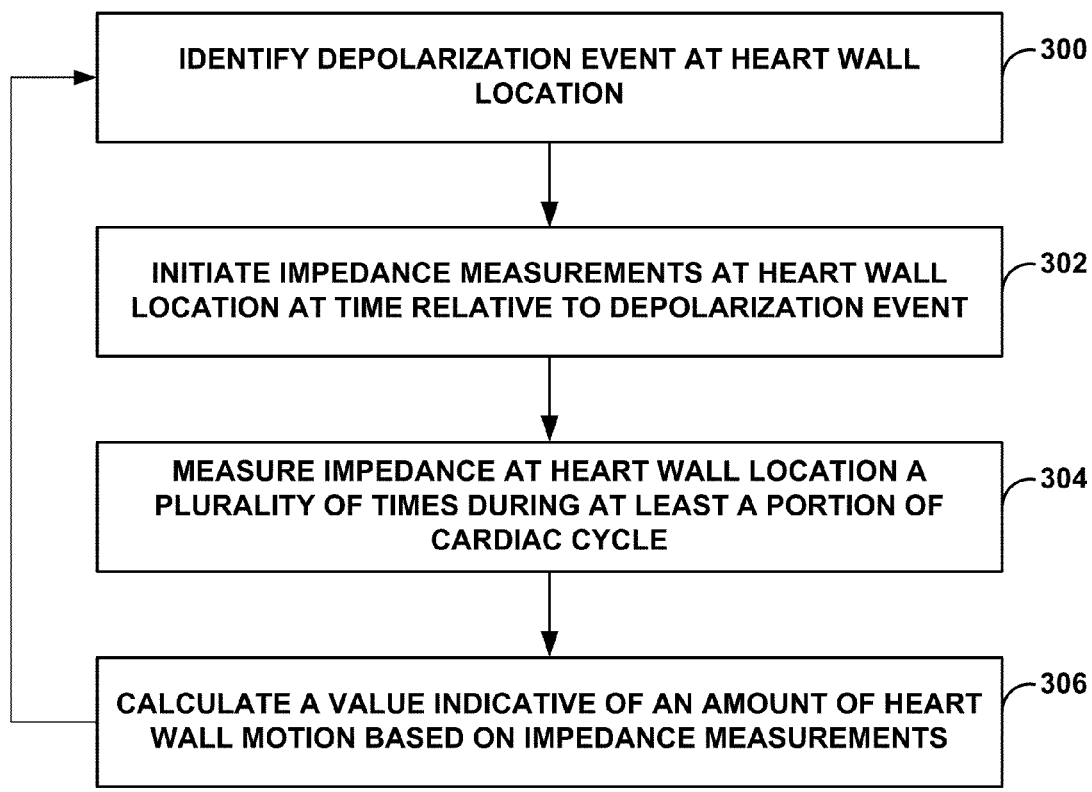
FIG. 12 is a flow diagram illustrating an example method of assessing cardiac wall motion using impedance measurements.

FIG. 12 depicts a flow diagram illustrating an example method of assessing cardiac wall motion using impedance measurements. The example method of FIG. 12 is described as being performed by IMD 16, e.g., processor 80 of IMD 16. In other examples, any one or more processors of any one or more devices described herein may individually or cooperatively perform the method of FIG. 12.

In the method illustrated in FIG. 12, processor 80 identifies a depolarization event at a heart wall location, e.g., a location at which impedance is to be measured to evaluate heart wall motion (300). The depolarization event may be delivery of a pacing pulse to the chamber in which the heart wall location is located, or an intrinsic depolarization, e.g., sensed via the lead that will be used for impedance measurements. In response to detection of the depolarization event, processor 80 initiates a plurality of impedance measurements for an electrical path that includes the heart wall location at a predetermined time relative to the depolarization event, e.g., a predetermined interval after the depolarization event, which may be stored a timing data 85 within memory 82 (302). Processor 80 controls signal generator 84 and impedance module 92 to perform the impedance measurements during at least a portion of the cardiac cycle, e.g., within a window beginning the predetermined interval after the depolarization event, which may correspond to the systolic phase of the cardiac cycle (304). Processor 80 calculates a value indicative of an amount of heart wall motion based on the impedance measurements, e.g., based on a difference between impedance measurements, or a rate of change of the impedance (306).

The method of FIG. 12 may be repeated, e.g., upon identification of each depolarization event at the heart wall location (300). Furthermore, the method of FIG. 12 may be performed for each of a plurality of heart wall locations by measuring the impedance of respective electrical paths including the heart wall locations a plurality of times. The impedance measurements for each heart wall location may be triggered by detection of a depolarization event for the respective location.

Figure 13:
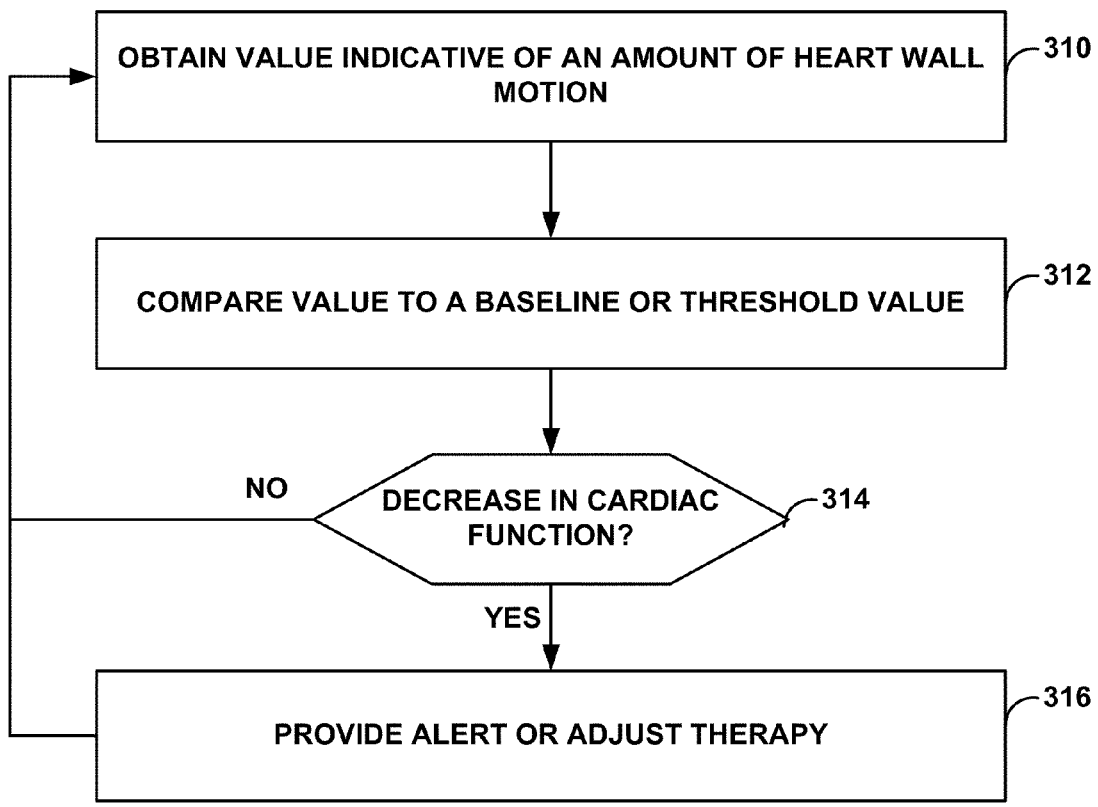
FIG. 13 is a flow diagram illustrating an example method monitoring cardiac function based on cardiac wall motion as assessed using impedance measurements.

FIG. 13 is a flow diagram illustrating an example method monitoring cardiac function based on cardiac wall motion as assessed using impedance measurements. The example method of FIG. 13 is described as being performed by IMD 16, e.g., processor 80 of IMD 16. In other examples, any one or more processors of any one or more devices described herein may individually or cooperatively perform the method of FIG. 13.

According to the example method of FIG. 13, processor 80 obtains a value indicative of an amount of heart wall motion, e.g., employing the method of FIG. 12 (310). Processor 80 may store this value as impedance data 83 within memory 82. Processor 80 compares the obtained value to a baseline or threshold value, which may be retrieved from impedance data 83 of memory 82 (312). The obtained value may be compared to a predetermined threshold, or a threshold determined based on previously obtained values indicative of heart wall motion, e.g., an average of previously obtained values, which may be recently obtained. In other examples, the obtained value may be compared to a baseline value determined based on values indicative of heart wall motion that were obtained at an earlier time, e.g., shortly after implant or another time when the patient was known to have a target cardiac function. Based on the comparison, processor 80 determines whether there has been a decrease in cardiac function warranting some action (314) and, if so, takes an action.

In the illustrated example, processor 80 provides an alert or adjusts a therapy if the comparison of the obtained value to the baseline or threshold value indicates a decrease in cardiac function (316). Processor 80 may provide an alert by activating an alarm, e.g., a speaker or mechanical actuator within IMD 16, or by transmitting an alert to programmer 24 or another device when in communication with the device, which device may in turn provide the alert to a user. Processor 80 may adjust a therapy, such as by adjusting timing intervals for CRT, switching pacing modes, or increasing/modifying delivery of neurostimulation or a therapeutic substance. In some examples, processor 80 may suggest modification of a therapy to user, e.g., via a message communicated to another device, e.g., programmer 24, and adjust therapy upon receiving a command or confirmation from the user via the other device.

The method of FIG. 13 may be performed for a signal heart wall location, or multiple heart wall locations. In examples involving multiple heart wall locations, the obtained values for the heart wall locations may be combined, e.g., summed or averaged, for comparison to the threshold or baseline value, or may be individually compared to the threshold or baseline value. In examples in which obtained values for different heart wall locations are individually compared to the baseline or threshold value, a decrease in cardiac function may be determined based on one of the comparisons, or may require multiple heart wall locations to indicate the decrease in cardiac function prior to providing an alert or adjusting a therapy.

Figure 14:
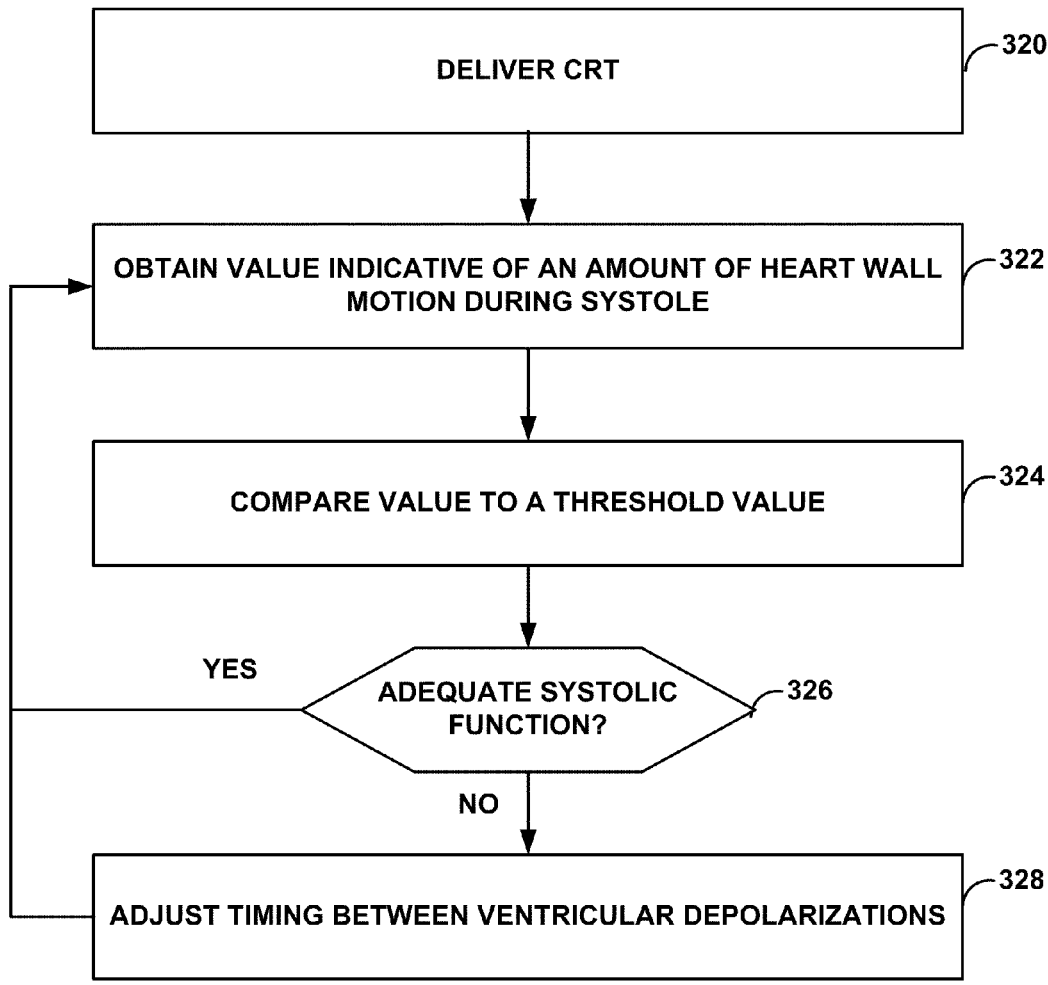
FIG. 14 is a flow diagram illustrating an example method of adjusting CRT based on cardiac wall motion as assessed using impedance measurements.

FIG. 14 is a flow diagram illustrating an example method of adjusting CRT based on cardiac wall motion as assessed using impedance measurements. The example method of FIG. 14 is described as being performed by IMD 16, e.g., processor 80 of IMD 16. In other examples, any one or more processors of any one or more devices described herein may individually or cooperatively perform the method of FIG. 14.

According to the example method of FIG. 14, IMD 16 delivers CRT to patient 14 (320). Processor 80 obtains a value indicative of an amount of heart wall motion during systole, e.g., employing the method of FIG. 12 based on impedance measurements obtained during a systolic portion of the cardiac cycle (322). Processor 80 compares the obtained value to a threshold value, which may be retrieved from impedance data 83 of memory 82 (324). The threshold value may represent a target indicative of adequate systolic function during CRT, e.g., a value desired as a result of CRT.

Based on the comparison, processor 80 determines whether the current configuration or programming of CRT is achieving adequate systolic function (326). If not, processor 80 adjusts the configuration or programming of CRT. In the illustrated example, processor 80 adjusts the timing between ventricular depolarizations, e.g., adjusts a V-V or one or more A-V intervals (328).

The method of FIG. 14 may be performed for a signal heart wall location, or multiple heart wall locations. In examples involving multiple heart wall locations, the obtained values for the heart wall locations may be combined, e.g., summed or averaged, for comparison to the threshold value, or may be individually compared to the threshold value. In examples in which obtained values for different heart wall locations are individually compared to the threshold value, a decrease in systolic function may be determined based on one of the comparisons, or may require multiple heart wall locations to indicate the decrease in systolic function prior to adjusting the CRT.

Figure 15:
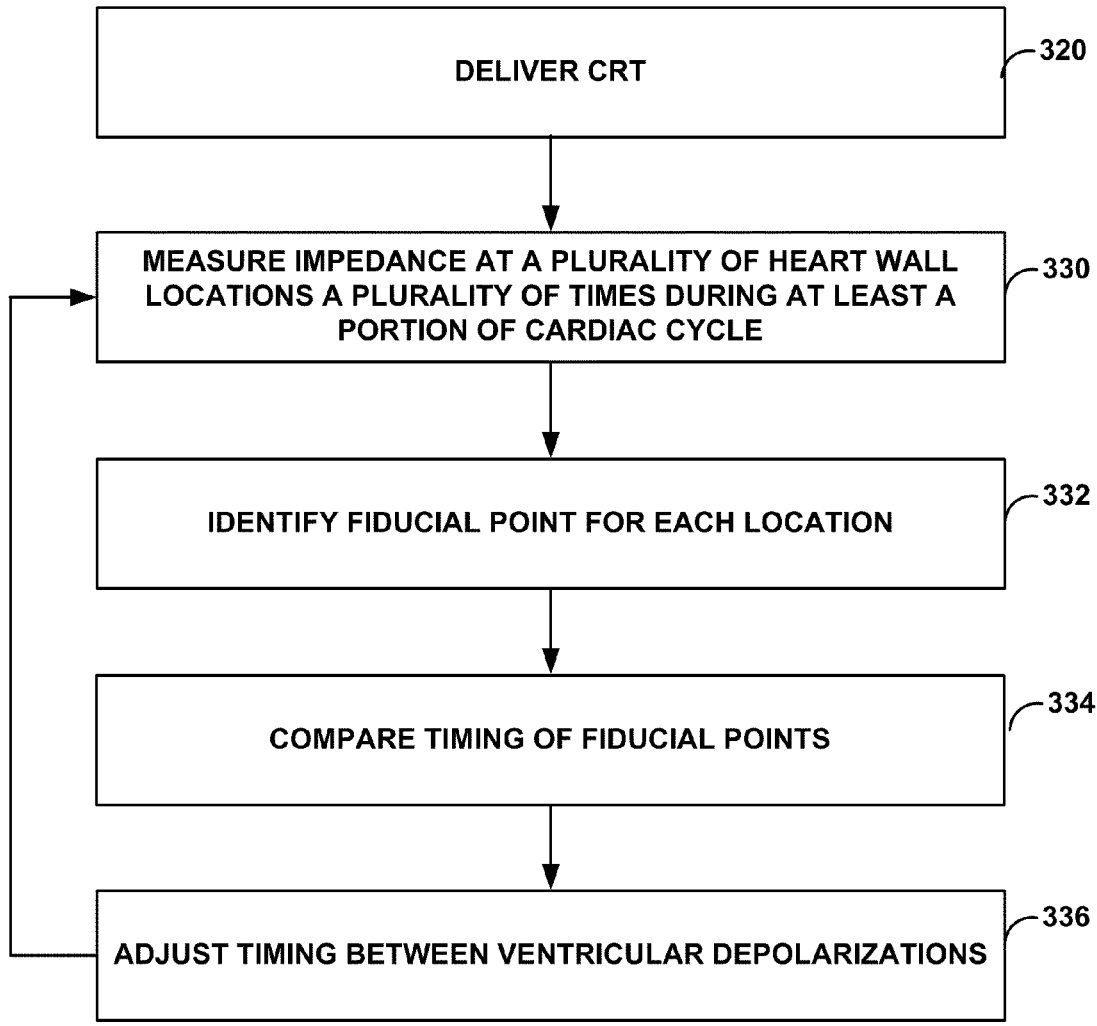
FIG. 15 is a flow diagram illustrating another example method of adjusting CRT based on cardiac wall motion as assessed using impedance measurements.

FIG. 15 is a flow diagram illustrating another example method of adjusting CRT based on cardiac wall motion as assessed using impedance measurements. The example method of FIG. 15 is described as being performed by IMD 16, e.g., processor 80 of IMD 16. In other examples, any one or more processors of any one or more devices described herein may individually or cooperatively perform the method of FIG. 15.

According to the example method of FIG. 15, IMD 16 delivers CRT to patient 14 (320). Processor 80 controls signal generator 84 and impedance module 92 to measure the impedance of each of a plurality of paths including a respective heart wall locations a plurality of times during at least a portion of a cardiac cycle, e.g., using the techniques discussed above with reference to FIG. 12. Processor 80 then identifies a fiducial point, e.g., onset of mechanical contraction, for each of the heart wall locations based on the measured impedances (332). Processor 80 compares the timing of the fiducial points for the different locations (334), and adjusts the timing between ventricular depolarizations based on the comparison (336).

Figure 16:
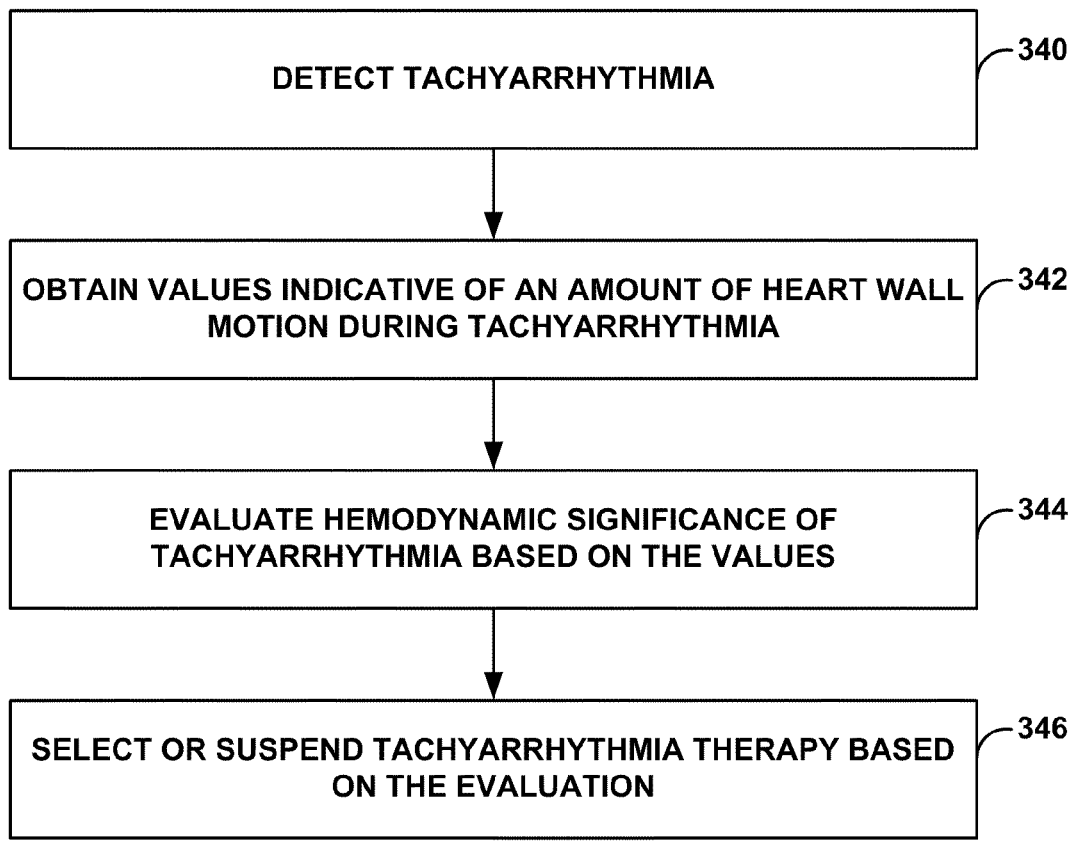
FIG. 16 is a flow diagram illustrating an example method of evaluating the hemodynamic significance of tachyarrhythmia based on cardiac wall motion as assessed using impedance measurements.

FIG. 16 is a flow diagram illustrating an example method of evaluating the hemodynamic significance of tachyarrhythmia based on cardiac wall motion as assessed using impedance measurements. The example method of FIG. 16 is described as being performed by IMD 16, e.g., processor 80 of IMD 16. In other examples, any one or more processors of any one or more devices described herein may individually or cooperatively perform the method of FIG. 16.

According to the example method of FIG. 16, processor 80 detects a tachyarrhythmia using any known technique, e.g., detects a ventricular tachyarrhythmia based on the lengths of consecutively detected R-R intervals (340). Processor 80 then obtains values indicative of an amount of heart wall motion during the tachyarrhythmia, e.g., using the example method of FIG. 12 (342). Processor 80 may obtain the values for one or more heart wall locations, and for one or more cardiac cycles.

Processor 80 evaluates the hemodynamic significance of the tachyarrhythmia based on the obtained values indicative of heart wall motion (344). For example, smaller and/or more variable difference or slope values may indicate a more hemodynamically significant, or dangerous, tachyarrhythmia. Processor 80 selects or suspends a tachyarrhythmia therapy based on the evaluation (346). For example, processor 80 may suspend or delay a defibrillation shock indicated by other analyses if the evaluation indicates that the tachyarrhythmia is less hemodynamically significant. In such situations, processor 80 may instead control delivery of ATP. Processor 80 may expedite or order a defibrillation shock if the evaluation indicates that the tachyarrhythmia is more hemodynamically significant.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Many examples of the disclosure have been described. These and other examples are within the scope of the following claims. Various modifications may be made without departing from the scope of the claims.

The invention claimed is:

1. A method comprising:
measuring an impedance of an electrical path that includes a portion of a heart wall a plurality of times during at least one portion of a cardiac cycle, the electrical path comprising a first electrode engaged to or within a wall of a chamber of a heart and a second electrode, wherein the second electrode is an extra-cardiac electrode that is disconnected from the heart; and
calculating a value indicative of heart wall motion during the portion of the cardiac cycle based on the impedance measurements.

2. The method of claim 1, wherein the value comprises a change in impedance during the at least one portion of the cardiac cycle.

3. The method of claim 1, wherein the value comprises a rate of change in impedance during the at least one portion of the cardiac cycle.

4. The method of claim 1, wherein the at least one portion of the cardiac cycle is a systolic period.

5. The method of claim 1, further comprising comparing the value to a previously stored value.

6. The method of claim 5, wherein the previously stored value is representative of a trend of values indicative of heart wall motion over time.

7. The method of claim 5, further comprising:
determining a change in cardiac contractility based upon the comparison.

8. The method of claim 5, further comprising:
assessing a hemodynamic significance of ventricular tachyarrhythmia based upon the comparison; and
determining whether to provide electrical stimulation therapy or adjust electrical stimulation therapy based upon the assessment.

9. The method of claim 5, further comprising:
adjusting a timing interval for cardiac resynchronization therapy based upon the comparison.

10. The method of claim 1, further comprising:
filtering the impedance measurements.

11. The method of claim 5, further comprising:
providing an alert based upon the comparison.

12. The method of claim 1, wherein the second electrode comprises one of a housing electrode of an implantable medical device or a superior vena cava coil electrode.

13. A system for assessing cardiac wall motion, the system comprising:
an impedance measurement module that measures an impedance of an electrical path that includes a portion of a heart wall a plurality of times during at least one portion of a cardiac cycle, the electrical path comprising a first electrode engaged to or within a wall of a chamber of a heart and a second electrode wherein the second electrode is an extra-cardiac electrode that is disconnected from the heart; and
a processor that is configured to:
calculate a value indicative of heart wall motion during the portion of the cardiac cycle based on the impedance measurements.

14. The system of claim 13, wherein the value comprises a change in impedance during the at least one portion of the cardiac cycle.

15. The system of claim 13, wherein the value comprises a rate of change in impedance during the at least one portion of the cardiac cycle.

16. The system of claim 13, wherein the at least one portion of the cardiac cycle is a systolic period.

17. The system of claim 13, wherein the processor is further configured to:
compare the value to a previously stored value.

18. The system of claim 17, wherein the previously stored value is representative of a trend of values indicative of heart wall motion over time.

19. The system of claim 17, wherein the processor is further configured to determine a change in cardiac contractility based upon the comparison.

20. The system of claim 17, wherein the processor is further configured to:
assess a hemodynamic significance of ventricular tachyarrhythmia based upon the comparison; and
determine whether to provide electrical stimulation therapy or adjust electrical stimulation therapy based upon the assessment.

21. The system of claim 17, wherein the processor is further configured to:
automatically adjust a timing cycle of an implantable device based on the comparison.

22. The system of claim 13, further comprising:
a filter that filters the impedance measurements.

23. The system of claim 13, wherein the processor is further configured to provide an alert based upon the comparison.

24. The system of claim 13, wherein the second electrode comprises one of a housing electrode of an implantable medical device or a superior vena cava coil electrode.

25. A device for assessing cardiac wall motion, the device comprising:
an impedance measurement module that measures an impedance of an electrical path that includes a portion of a heart wall a plurality of times during at least one portion of a cardiac cycle, the electrical path comprising a first electrode engaged to or within a wall of a chamber of a heart and a second electrode wherein the second electrode is an extra-cardiac electrode that is disconnected from the heart; and
a processor that is configured to:
calculate a value indicative of heart wall motion during the portion of the cardiac cycle based on the impedance measurements.

26. The device of claim 25, wherein the value comprises a change in impedance during the at least one portion of the cardiac cycle.

27. The device of claim 25, wherein the value comprises a rate of change in impedance during the at least one portion of the cardiac cycle.

28. The device of claim 25, wherein the at least one portion of the cardiac cycle is a systolic period.

29. The device of claim 25, wherein the processor is further configured to:
compare the value to a previously stored value.

30. The device of claim 29, wherein the previously stored value is representative of a trend of values indicative of heart wall motion over time.

31. The device of claim 29, wherein the processor is further configured to determine a change in cardiac contractility based upon the comparison.

32. The device of claim 29, wherein the processor is further configured to:
assess a hemodynamic significance of ventricular tachyarrhythmia based upon the comparison; and
determine whether to provide electrical stimulation therapy or adjust electrical stimulation therapy based upon the assessment.

33. The device of claim 29, wherein the processor is further configured to:
automatically adjust a timing cycle of an implantable device based on the comparison.

34. The device of claim 25, further comprising:
a filter that filters the impedance measurements.

35. The device of claim 25, wherein the processor is further configured to provide an alert based upon the comparison.

36. The device of claim 25, wherein the second electrode comprises one of a housing electrode of an implantable medical device or a superior vena cava coil electrode.

37. A non-transitory computer-readable storage medium comprising instructions encoded on the computer-readable medium that, upon execution, cause a processor within an implantable medical device to:
measure an impedance of an electrical path that includes a portion of a heart wall a plurality of times during at least one portion of a cardiac cycle, the electrical path comprising a first electrode engaged to or within a wall of a chamber of a heart and a second electrode, wherein the second electrode is an extra-cardiac electrode that is disconnected from the heart; and
calculate a value indicative of heart wall motion during the portion of the cardiac cycle based on the impedance measurements.

* * * * *